(12) United States Patent
Chen et al.

(10) Patent No.: US 11,590,077 B2
(45) Date of Patent: Feb. 28, 2023

(54) FULVESTRANT FORMULATIONS AND METHODS OF THEIR USE

(71) Applicant: EAGLE PHARMACEUTICALS, INC., Woodcliff Lake, NJ (US)

(72) Inventors: Feng-Jing Chen, Irvine, CA (US); Steven L. Krill, Midland Park, NJ (US); Rama Abu Shmeis, Branchburg, NJ (US); Adrian Hepner, Ramsey, NJ (US); Charles Wescott, Woodcliff Lake, NJ (US); Tara Jaskowski, Woodcliff Lake, NJ (US); Michael Joyce, Woodcliff Lake, NJ (US)

(73) Assignee: Eagle Pharmaceuticals, Inc., Woodcliff Lake, NJ (US)

( * ) Notice: Subject to any disclaimer, the term of this patent is extended or adjusted under 35 U.S.C. 154(b) by 97 days.

(21) Appl. No.: 16/762,229

(22) PCT Filed: Nov. 8, 2018

(86) PCT No.: PCT/US2018/059906
§ 371 (c)(1),
(2) Date: May 7, 2020

(87) PCT Pub. No.: WO2019/094650
PCT Pub. Date: May 16, 2019

(65) Prior Publication Data
US 2020/0360284 A1    Nov. 19, 2020

Related U.S. Application Data

(60) Provisional application No. 62/583,403, filed on Nov. 8, 2017.

(51) Int. Cl.
*A61K 9/10* (2006.01)
*A61K 31/566* (2006.01)
(Continued)

(52) U.S. Cl.
CPC ............. *A61K 9/10* (2013.01); *A61K 9/0019* (2013.01); *A61K 31/519* (2013.01);
(Continued)

(58) Field of Classification Search
None
See application file for complete search history.

(56) References Cited

U.S. PATENT DOCUMENTS

| 6,774,122 B2 | 8/2004 | Evans et al. |
| 2003/0114430 A1* | 6/2003 | MacLeod ............... A61P 5/32 514/182 |
| 2008/0161276 A1 | 7/2008 | Johnsson et al. |

FOREIGN PATENT DOCUMENTS

| CN | 101525364 A | 9/2009 |
| EP | 1250138 A1 | 10/2002 |

(Continued)

Primary Examiner — Melissa S Mercier
(74) Attorney, Agent, or Firm — BakerHostetler

(57) ABSTRACT

The present disclosure provides methods of treating breast cancer including administering aqueous suspensions comprising solubilized fulvestrant, non-solubilized fulvestrant particles having one or more of an LD Dv(10) between about 1.5 and about 2.1 microns, an LD Dv(50) between about 5.5 and about 9.0 microns, and an LD Dv(90) between about 15 and about 35 microns, with the aqueous suspensions further including a surfactant, a polyvinylpyrrolidone, and a sugar alcohol, and a water-soluble excipient. The water-soluble excipient can be an aryl-Ci-6alk-OH, a Ci-6alkyl-OH, a buffering salt, a polysorbate, a polyalkylene glycol, a Ci-i2alkylene glycol, a phosphatidylcholine, or a combination thereof.

56 Claims, 7 Drawing Sheets

(51) Int. Cl.
   *A61K 47/32*   (2006.01)
   *A61K 47/24*   (2006.01)
   *A61K 9/00*    (2006.01)
   *A61K 31/519*  (2006.01)
   *A61K 47/26*   (2006.01)

(52) U.S. Cl.
   CPC ............ *A61K 31/566* (2013.01); *A61K 47/24* (2013.01); *A61K 47/26* (2013.01); *A61K 47/32* (2013.01)

(56) References Cited

FOREIGN PATENT DOCUMENTS

| | | |
|---|---|---|
| EP | 2460539 A1 | 6/2012 |
| WO | 01/51056 A1 | 7/2001 |
| WO | 03/06064 | 1/2003 |
| WO | 2012/035516 A1 | 3/2012 |
| WO | 2013/153559 A1 | 10/2013 |
| WO | 2013/182668 A1 | 12/2013 |
| WO | 2015/033302 A2 | 3/2015 |
| WO | 2017/193048 A1 | 11/2017 |

\* cited by examiner

FULVESTRANT FORMULATIONS AND METHODS OF THEIR USE

CROSS REFERENCE TO RELATED APPLICATIONS

This application is a National Stage Application filed under 35 U.S.C. 371 of International Application No. PCT/US2018/059906, filed Nov. 8, 2018, which claims the benefit of U.S. Provisional Application No. 62/583,403, filed Nov. 8, 2017, the entirety of which is incorporated by reference herein.

FIELD

The disclosure is directed to fulvestrant-containing formulations and methods of their use in the treatment of disease.

BACKGROUND

Fulvestrant, or 7-(9-(4,4,5,5,5-pentafluoropentylsulfinyl)nonyl) estra-1,3,5(10)-triene-3,17-diol, has the structure of formula (1):

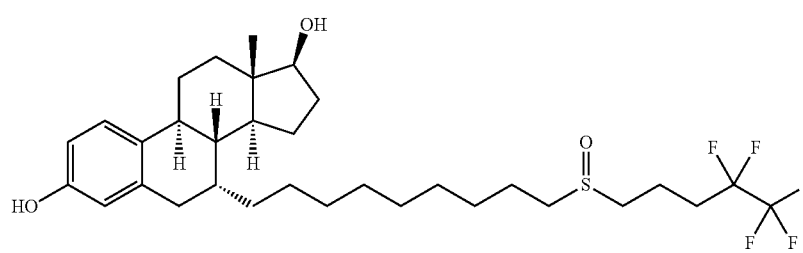

(1)

Fulvestrant is a selective estrogen receptor degrader (SERD) indicated for the treatment of hormone receptor positive metastatic breast cancer in postmenopausal women with disease progression following anti-estrogen therapy.

As with other steroidal-like compounds, fulvestrant has physical properties that make preparing aqueous suspensions difficult. Fulvestrant is a particularly lipophilic molecule, even when compared with other steroidal compounds, and its aqueous solubility is extremely low.

Due to the poor solubility and oral bioavailability of fulvestrant, the drug is currently administered via intramuscular injection of an oil-based fulvestrant formulation. The current commercial formulation of fulvestrant, FASLODEX®, is dosed at 500 mg and requires that two 5 mL injections of a 50 mg/mL fulvestrant formulation be administered intramuscularly. Each 5 mL injection contains 10% w/v alcohol, 10% w/v benzyl alcohol, and 15% w/v benzyl benzoate as co-solvents and made up to 100% w/v with castor oil as a further co-solvent and release rate modifier. Administration of the formulation is slow (1-2 minutes per injection) and painful, due to the viscous oil-based vehicle used to solubilize fulvestrant. A warning has been added to the FASLODEX® label concerning painful injections, sciatica, neuropathic pain, and peripheral neuropathy.

It has been previously reported (U.S. Pat. No. 6,774,122 to AstraZeneca) that intramuscular injections of fulvestrant in the form of an aqueous suspension were not suitable for use. Those suspensions resulted in extensive local tissue irritation at the injection site as well as a poor release profile due to the presence of fulvestrant in the form of solid particles. Furthermore, the fulvestrant release rate was reported as not clinically significant.

There is a need for fulvestrant formulations with improved dosing properties. The disclosure is directed to these and other important needs.

SUMMARY

The present disclosure provides aqueous suspensions comprising solubilized fulvestrant, non-solubilized fulvestrant particles having one or more of an LD Dv(10) between about 1.5 and about 2.1 microns, an LD Dv(50) between about 5.5 and about 9.0 microns, and an LD Dv(90) between about 15 and about 35 microns, the aqueous suspensions further comprising a surfactant, a polyvinylpyrrolidone, and a sugar alcohol, and a water-soluble excipient. The water-soluble excipient can be an aryl-$C_{1-6}$alk-OH, a $C_{1-6}$alkyl-OH, a buffering salt, a polysorbate, a polyalkylene glycol, a $C_{1-12}$alkylene glycol, a phosphatidylcholine, or a combination thereof.

The present disclosure provides methods of treating breast cancer in a subject, comprising administering to the subject the aqueous suspensions of the disclosure. The breast cancer can be hormone receptor (HR)-positive breast cancer.

Methods of making and using the products described herein are also described.

BRIEF DESCRIPTION OF THE DRAWINGS

The summary, as well as the following detailed description, is further understood when read in conjunction with the appended drawings. For the purpose of illustrating the disclosure, there are shown in the drawings exemplary embodiments of the disclosure; however, the disclosure is not limited to the specific methods, compositions, and devices disclosed. In the drawings.

Figure 1:
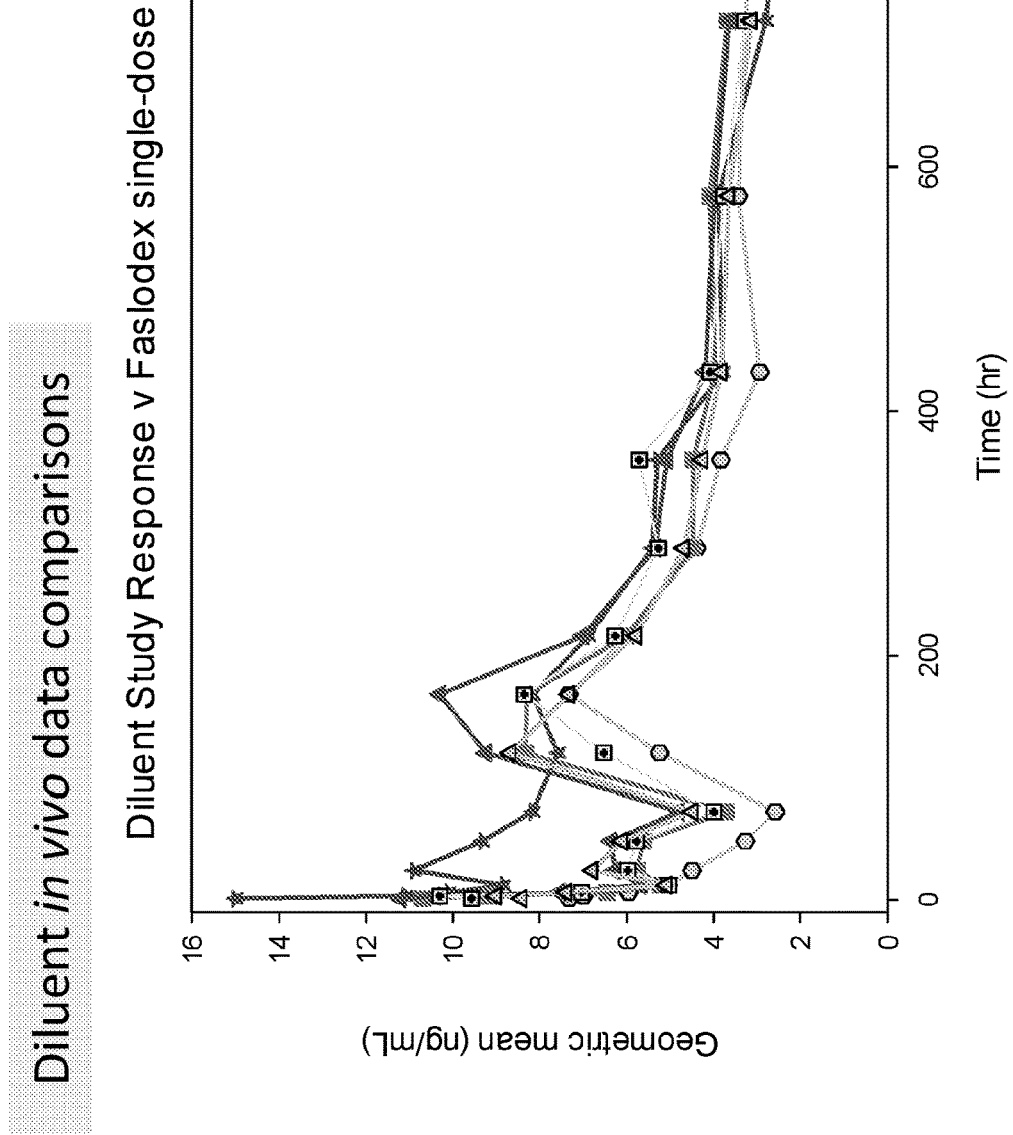
FIG. 1 depicts pharmacokinetic data for administration of commercial fulvestrant formulations (FASLODEX®) and some exemplary aqueous suspensions of the present disclosure to rats.
Figure 2:
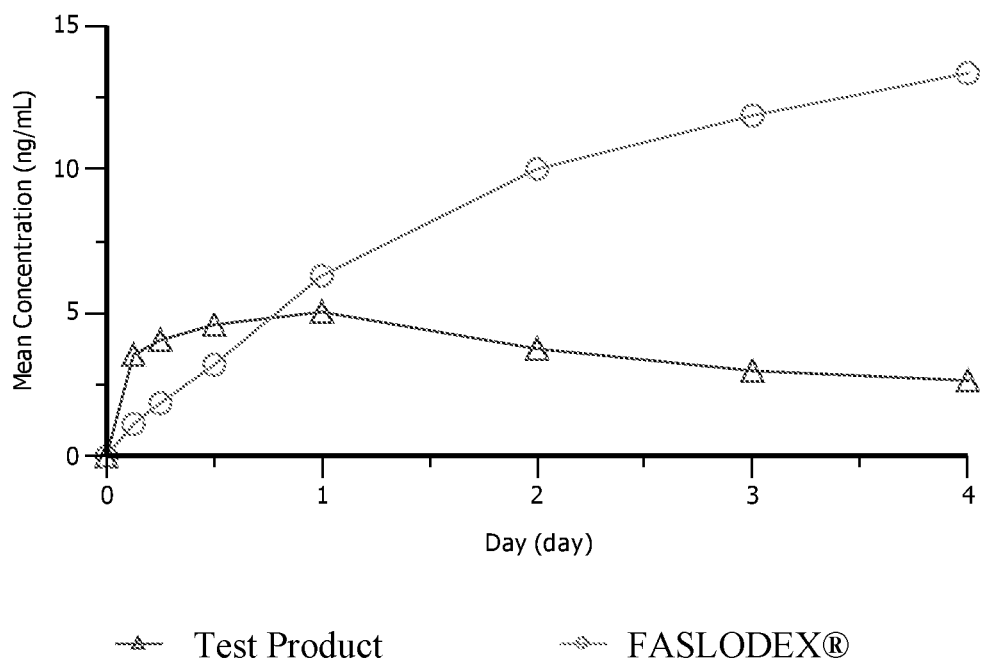
FIG. 2 depicts pharmacokinetic data for administration of commercial fulvestrant formulations (FASLODEX®) and an exemplary aqueous suspension of the present disclosure to humans.
Figure 3:
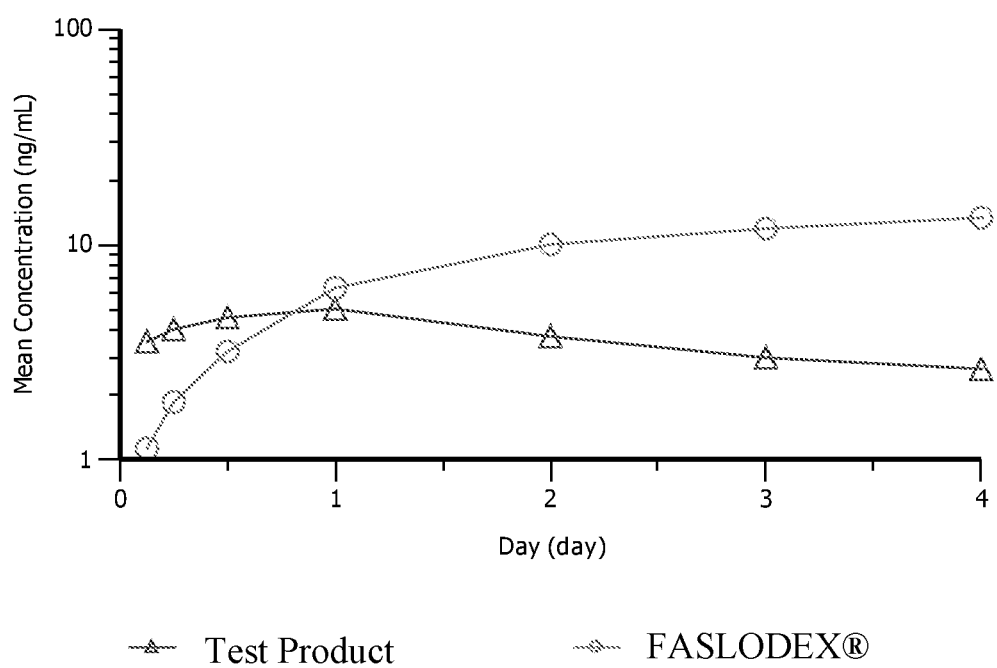
FIG. 3 depicts pharmacokinetic data for administration of commercial fulvestrant formulations (FASLODEX®) and an exemplary aqueous suspension of the present disclosure to humans.
Figure 4:
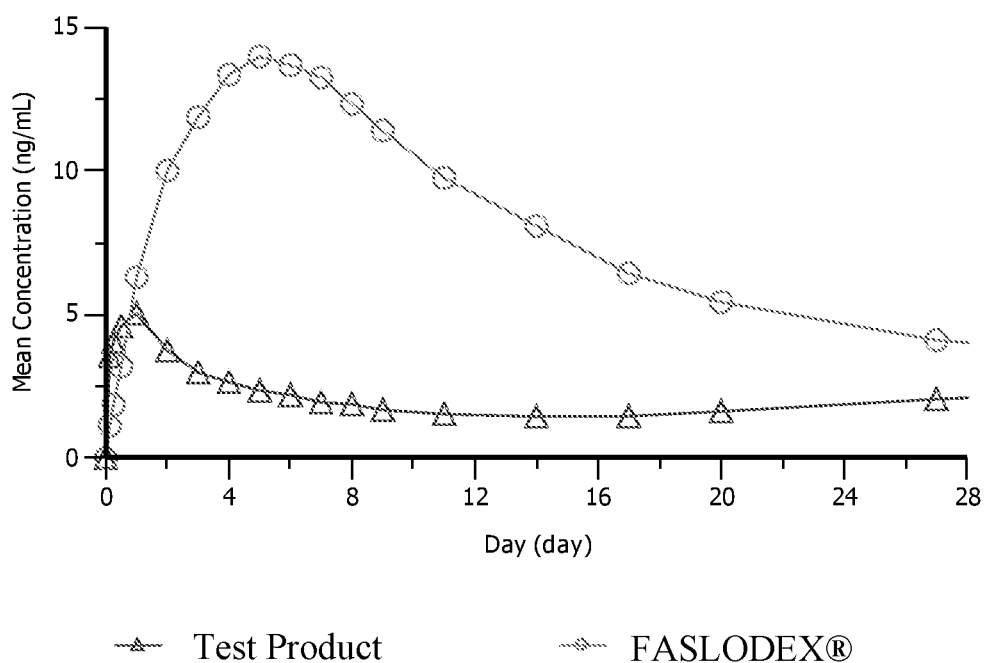
FIG. 4 depicts pharmacokinetic data for administration of commercial fulvestrant formulations (FASLODEX®) and an exemplary aqueous suspension of the present disclosure to humans.
Figure 5:
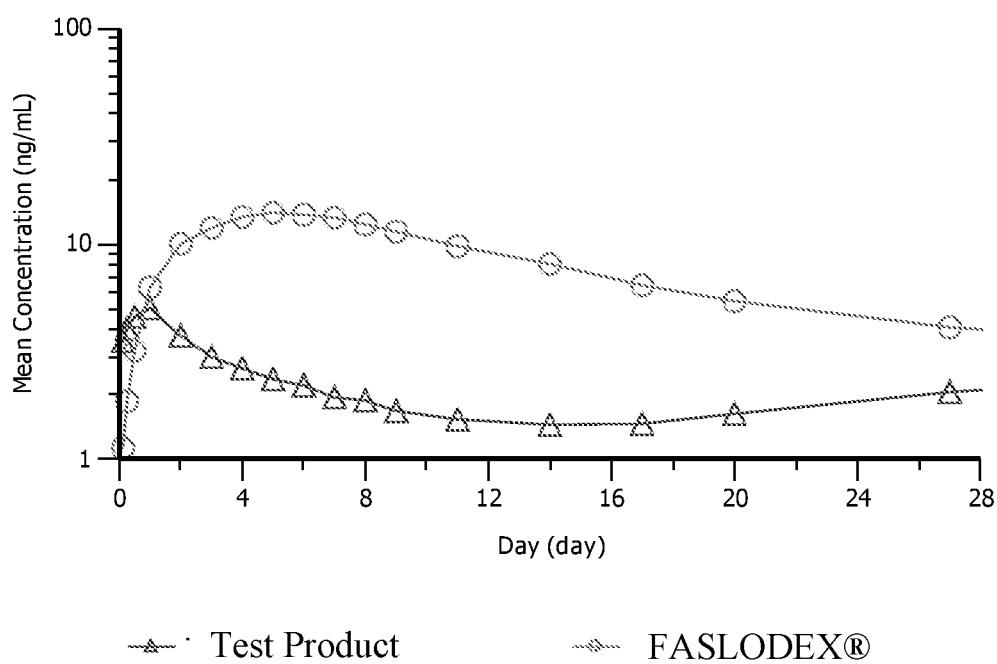
FIG. 5 depicts pharmacokinetic data for administration of commercial fulvestrant formulations (FASLODEX®) and an exemplary aqueous suspension of the present disclosure to humans.
Figure 6:
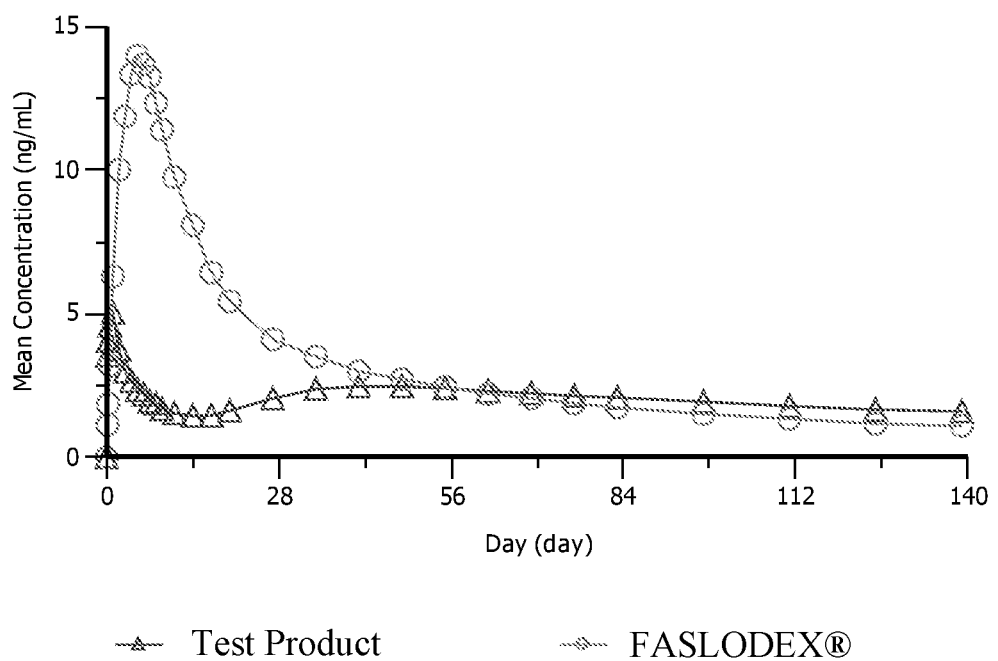
FIG. 6 depicts pharmacokinetic data for administration of commercial fulvestrant formulations (FASLODEX®) and an exemplary aqueous suspension of the present disclosure to humans.
Figure 7:
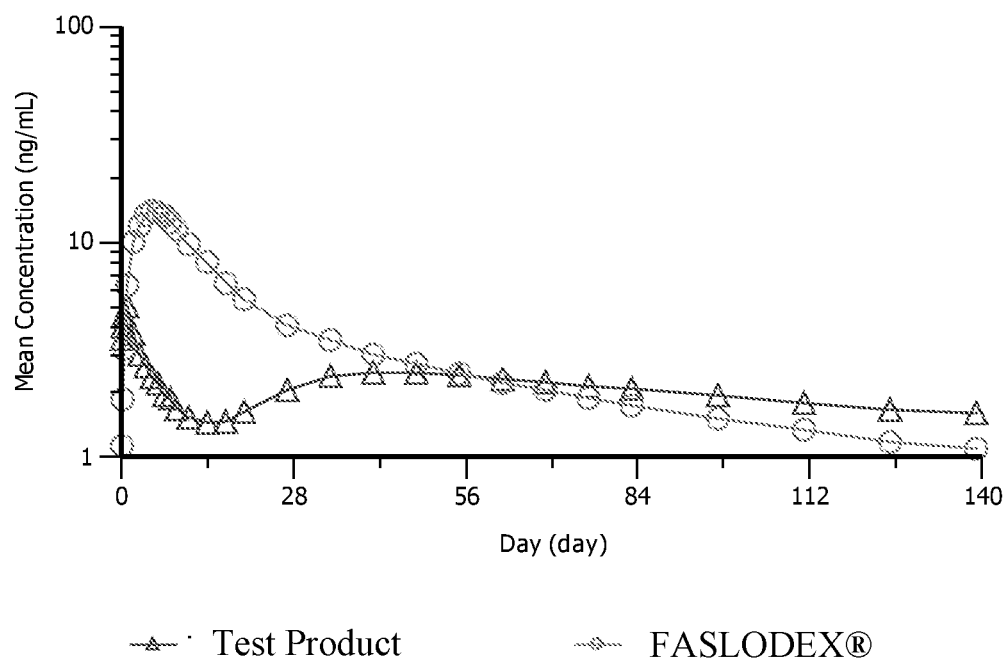
FIG. 7 depicts pharmacokinetic data for administration of commercial fulvestrant formulations (FASLODEX®) and an exemplary aqueous suspension of the present disclosure to humans.

All callouts and annotations in the Figures are hereby incorporated into this description as if fully set forth herein

DETAILED DESCRIPTION OF ILLUSTRATIVE EMBODIMENTS

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the claimed disclosure.

As used in the specification including the appended claims, the singular forms "a," "an," and "the" include the plural, and reference to a particular numerical value includes at least that particular value, unless the context clearly dictates otherwise.

When a range of values is expressed, another embodiment includes from the one particular value and/or to the other particular value. All ranges are inclusive and combinable. Further, reference to values stated in ranges include each and every value within that range. When values are expressed as approximations, by use of the antecedent "about," it will be understood that the particular value forms another embodiment. The term "about" as used herein when referring to a measurable value such as an amount, a temporal duration, and the like, is meant to encompass reasonable variations of the value, such as, for example, +10% from the specified value. For example, the phrase "about 50%" can include 10% of 50, or from 45% to 55%.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination.

Terms

As used herein, whether by itself or in conjunction with another term or terms, it should be understood that the phrases "method of treating" and "method of treatment" may be used interchangeably with the phrase "for use in the treatment of" a particular disease.

As used herein, whether by itself or in conjunction with another term or terms, "pharmaceutically acceptable" indicates that the designated entity such as, for example, e.g., a pharmaceutically acceptable excipient is generally chemically and/or physically compatible with other ingredients in a formulation, and/or is generally physiologically compatible with the recipient thereof.

As used herein, whether by themselves or in conjunction with another term or terms, "subject(s)," "individual(s)," and "patient(s)", refer to mammals, including humans. The term human(s) refers to and includes, a human child, adolescent, or adult.

As used herein, whether by themselves or in conjunction with another term or terms, "treats," "treating," "treated," and "treatment," refer to and include ameliorative, palliative, and/or curative uses and results, or any combination thereof. In other embodiments, the methods described herein can be used prophylactically. It should be understood that "prophylaxis" or a prophylactic use or result do not refer to nor require absolute or total prevention (i.e., a 100% preventative or protective use or result). As used herein, prophylaxis or a prophylactic use or result refer to uses and results in which administration of a compound or formulation diminishes or reduces the severity of a particular condition, symptom, disorder, or disease described herein; diminishes or reduces the likelihood of experiencing a particular condition, symptom, disorder, or disease described herein; or delays the onset or relapse (reoccurrence) of a particular condition, symptom, disorder, or disease described herein; or any combination of the foregoing.

As used herein, whether used alone or in conjunction with another term or terms, "therapeutic" and "therapeutically effective amount", refer to an amount of a compound or formulation that (a) treats a particular condition, symptom, disorder, or disease described herein; (b) attenuates, ameliorates or eliminates one or more symptoms of a particular condition, disorder, or disease described herein; (c) delays the onset or relapse (reoccurrence) of a particular condition, symptom, disorder, or disease described herein. It should be understood that the terms "therapeutic" and "therapeutically effective" encompass any one of the aforementioned effects (a)-(c), either alone or in combination with any of the others (a)-(c).

As used herein, whether used alone or in conjunction with another term or terms, "therapeutic agent" refers to any substance included in a formulation that is useful in the treatment of a disease, condition, or disorder or comorbidity (i.e., a disease, condition, or disorder that exists simultaneously with breast cancer) and is not fulvestrant.

As used herein, whether used alone or in conjunction with another term or terms, "suspension" refers to solid particles dispersed in a liquid vehicle. As used herein, whether used alone or in conjunction with another term or terms, "aqueous suspension" refers to a suspension in which the liquid vehicle comprises at least about 50% w/w water. As used herein, whether used alone or in conjunction with another term or terms, a "vehicle" is a suspending medium, preferably a pharmaceutically acceptable suspending medium.

As used herein, whether alone or in conjunction with another term or terms, "dose" and "dosage" refers to an amount of fulvestrant in an aqueous suspension.

As used herein, whether alone or in conjunction with another term or terms, "aryl" when used alone or as part of a substituent group refers to a mono- or bicyclic-aromatic hydrocarbon ring structure having 6 to 10 carbon atoms in the ring. Preferred aryl moieties include phenyl and naphthyl.

As used herein, whether alone or in conjunction with another term or terms, "$C_1$-$C_6$alk" when used alone or as part of a substituent group refers to an aliphatic linker having 1, 2, 3, 4, 5, or 6 carbon atoms and includes, for example, —$CH_2$—, —$CH(CH_3)$—, —$CH(CH_3)$—$CH_2$—, and —$C(CH_3)_2$—. The term "—$C_0$alk-" refers to a bond.

As used herein, whether alone or in conjunction with another term or terms, "alkyl," when used alone or as part of a substituent group, refers to a straight- or branched-chain hydrocarbon group having from 1 to 12 carbon atoms ("$C_1$-$C_{12}$"), preferably 1 to 6 carbons atoms ("$C_1$-$C_6$"), in the group. Examples of alkyl groups include methyl (Me, $C_1$alkyl), ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and the like.

When a range of carbon atoms is used herein, for example, $C_1$-$C_6$, all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$.

As used herein "Dv(10)", "Dv(50)" and "Dv(90)" are defined as the volume weighted particle diameters where a cumulative 10%, 50% or 90% v/v of the particles have an equal or smaller diameter, respectively, when measured. For example, if a particle population has a Dv(50) of about 25 microns, 50% of the particles in volume have a diameter of less than or equal to about 25 microns.

As used herein, Dn(10)", "Dn(50)" and "Dn(90)" are defined as the number weighted particle diameters where a cumulative 10%, 50% or 90% of the particles have an equal or smaller diameter, respectively, when measured. For example, if a particle population has a Dn(50) of about 25 microns, 50% of the particles in number have a diameter of less than or equal to about 25 microns.

Particle size and particle size distributions can be determined by measurement via laser diffraction. Particle size analysis by laser diffraction methods is known in the art and is explained more fully by ISO 13320:2009(E), "Particle size analysis—Laser diffraction methods," International Organization for Standardization which is incorporated by reference herein in its entirety for all purposes. Particle sizes determined by laser diffraction are represented as the diameter of a sphere having equivalent volume to the particle volume as determined by Mie theory of light scattering. Measurements via laser diffraction may be obtained "as is" or "sonicated." Values measured via laser diffraction "as is" are indicated as such in the Tables, or are referred to herein by "laser diffraction Dv(##)", "LD Dv(##)", "laser diffraction diameter", or "LD diameter." Data for "sonicated" samples indicates that the measurement sample was subjected to sonication to disperse agglomerates immediately prior to analysis, as more fully described in ISO 13320:2009 (E). Values measured via laser diffraction for samples subjected to sonication are specifically referred to herein by "sonicated laser diffraction Dv(##)", sonicated "LD Dv(##)", "sonicated laser diffraction diameter", or "sonicated LD diameter.". Tables 3-6 provide laser diffraction particle size and particle size distribution ("PSD") data for some exemplary embodiments of the present invention.

Particle size and particle size distributions can also be determined by microscopy image capture and analysis. Microscopy image capture and analysis captures a two dimensional (2D) image of a 3D particle and calculates various size and shape parameters from the 2D image. Particle sizes determined by microscopy image capture and analysis are represented as the diameter of a circle with the equivalent area as the 2D image of the particle, referred to herein as a circle equivalent or "CE" diameter. Particle size analysis by microscopy image capture and analysis is known in the art and is explained more fully by ISO 13322-1:2014, "Particle size analysis—Image analysis methods—Part 1: Static image analysis methods," International Organization for Standardization, which is incorporated by reference herein in its entirety for all purposes. Values measured by microscopy image capture and analysis are referred to herein by "circle equivalent diameter," "CE diameter," "circle equivalent Dv(##)," "CE Dv(##)", or "CE Dn(##)". Table 6 provides microscopy image capture and analysis particle size and particle size distribution data for some exemplary embodiments of the present invention.

Aqueous Suspensions

In particular embodiments, the disclosure is directed to aqueous suspensions comprising solubilized fulvestrant and non-solubilized fulvestrant particles. The non-solubilized fulvestrant particles may have different particle size distributions as described more fully elsewhere herein. In some embodiments, aqueous suspensions of the disclosure can have a total concentration of fulvestrant from solubilized fulvestrant and non-solubilized fulvestrant of about 80 mg/mL to about 170 mg/mL, including all ranges and subranges there between. In other embodiments, the total concentration of fulvestrant is about 75 mg/mL to about 125 mg/mL. In particular embodiments, the total concentration of fulvestrant is about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, or about 170 mg/mL. In still further embodiments, the total concentration of fulvestrant is about 100 mg/mL.

The aqueous suspensions of the disclosure comprise solubilized fulvestrant, that is, fulvestrant that is present in non-particulate form and that may be dissolved in the aqueous medium of the suspension. In some embodiments of the invention, the aqueous suspensions can have between about 0.01 mg/mL and about 0.10 mg/mL, between about 0.05 mg/mL and about 0.10 mg/mL, between about 0.05 mg/mL and about 0.08 mg/mL, or about 0.06 mg/mL of the solubilized fulvestrant. For example, the aqueous suspensions can have 0.01, 0.02, 0.03, 0.04, 0.05, 0.06, 0.07, 0.08, 0.09, or 0.1 mg/mL of the solubilized fulvestrant.

In certain embodiments of the invention, the aqueous suspensions comprising solubilized fulvestrant and non-solubilized fulvestrant particles also comprise a surfactant, a polyvinylpyrrolidone, a sugar alcohol, and a water-soluble excipient.

In some embodiments of the invention, the surfactants can be, but are not limited to, polyethylene oxide (PEO), a PEO derivative, polysorbate 80, polysorbate 20, poloxamer 188 (including, but not limited to, PLURONIC® F-68 poloxamer sold by BASF Corp. (Wyandotte, Mich., USA)), poloxamer 124 (including, but not limited to, PLURONIC® L44 poloxamer sold by BASF Corp. (Wyandotte, Mich., USA)), poloxamer 407 (including, but not limited to, PLURONIC® F127 poloxamer sold by BASF Corp. (Wyandotte, Mich., USA)), polyethoxylated vegetable oils, polyethoxylated castor oil (including but not limited to KOLLIPHOR® EL, formerly known as CREMOPHOR® EL sold by BASF Corp. (Wyandotte, Mich., USA)), sorbitan palmitate (including, but not limited to, SPAN™ 40 sold by Croda International Plc), lecithin, poly(vinyl alcohol) ("PVA"), human serum albumin, and mixtures thereof.

In some embodiments of the invention, the polyvinylpyrrolidones can be, but are not limited to, povidone K12, povidone K17, PLASDONE™ C-12 povidone (Ashland, Inc., Covington, Ky., USA), PLASDONE™ C-17 povidone (Ashland, Inc., Covington, Ky., USA), PLASDONE™ C-30 povidone (Ashland, Inc., Covington, Ky., USA), and mixtures thereof. In certain embodiments of the invention, the polyvinylpyrrolidone is PLASDONE™ C-12 povidone, which has a K value of 10.2-13.8 and nominal molecular weight of 4,000 daltons.

In some embodiments of the invention, the sugar alcohols can be, but are not limited to, dextrose, glycerol, mannitol, erythritol, threitol, arabitol, xylitol, ribitol, sorbitol, galactitol, fucitol, iditol, inositol, volemitol, isomalt, maltitol, lactitol, maltotriitol, maltotetraitol, polyglycitol, and mixtures thereof. In further embodiments of the invention, the sugar alcohol is mannitol, xylitol, maltitol, lactitol, maltotriitol, sorbitol, glycerol, or a mixture thereof. In yet further embodiments of the invention, the sugar alcohol is mannitol.

According to the disclosure, the aqueous suspensions comprise a water-soluble excipient can be an aryl-$C_{1-6}$alk-OH, a $C_{1-6}$alkyl-OH, a buffering salt, a polysorbate, a polyalkylene glycol, a $C_{1-12}$alkylene glycol, a phosphatidylcholine, or a combination thereof.

In certain embodiments of the invention, the aqueous suspensions of the disclosure comprise between about 0.1% and about 5% (w/w), between about 0.5% and about 5% (w/w), between about 0.5% and about 2.5% (w/w), between about 0.9% and about 1.5% (w/w), about 4% (w/w), or about 1% (w/w) of the aryl-$C_{1-6}$alk-OH. For example, the aqueous suspensions can comprise 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5% (w/w) of the aryl-$C_{1-6}$alk-OH The aryl-$C_{1-6}$alk-OH is preferably a phenyl-$C_{1-6}$alk-OH, for example, a phenyl-$C_{1-2}$—OH. In further embodiments, the aryl-$C_{1-6}$alk-OH is benzyl alcohol (phenyl-$CH_2$—OH).

In certain embodiments of the invention, the aqueous suspensions comprise between about 1% and about 10% (w/w), between about 5% and about 10% (w/w), between about 2% and about 4% (w/w), about 2% (w/w), about 4% (w/w), about 5% (w/w), or about 8% (w/w) of the $C_{1-6}$alkyl-OH. For example, the aqueous suspensions can comprise about 1, 1.5, 2, 2.5, 3, 3.5, 4, 4.5, 5, 5.5, 6, 6.5, 7, 7.5, 8, 8.5, 9, 9.5, or 10% (w/w) of the $C_{1-6}$alkyl-OH. Preferred $C_{1-6}$alkyl-OH include methanol, ethanol, propanol, isopropanol, butanol, s-butanol, t-butanol, and combinations thereof. In further embodiments, the $C_{1-6}$alkyl-OH is ethanol.

In certain embodiments of the invention, the aqueous suspensions of the disclosure comprise one or more buffering salts, which can be an agent that when added to an aqueous suspension, results in an aqueous suspension that resists pH changes or that results in a change in pH. According to the disclosure, pH is mentioned using conventional instrumentation at ambient temperature, e.g., between 20° C. and 25° C., preferably 23° C. The buffering salt can be, for example, a sodium phosphate salt (e.g, $NaH_2PO_4 \cdot H_2O$, $NaH_2PO_4 \cdot 2H_2O$, anhydrous $NaH_2PO_4$), a potassium phosphate salt (e.g., potassium phosphate dibasic ($K_2HPO_4$), potassium phosphate monobasic ($KH_2PO_4$)), citric acid or a salt thereof (e.g., sodium citrate), tromethane (tris(hydroxymethyl) aminomethane, "Tris"), or a mixture thereof. In certain embodiments of the invention, the aqueous suspension comprises about 1 mM to 20 mM, of buffering salts, and all ranges and subranges therebetween. In particular embodiments of the invention, the aqueous suspension comprises about 1 to 2 mM, 1 to 3 mM, 1 to 5 mM, 2 to 8 mM, 5 to 6 mM, 5 to 10 mM, 8 to 12 mM, 10 to 15 mM, or 15 to 20 mM of one or more buffering salts, and all ranges and subranges there between. In further embodiments of the invention, the aqueous suspension comprises about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, or 20 mM of one or more buffering salts.

In certain embodiments of the invention, the aqueous suspensions can comprise between about 0.1% to about 2% (w/w), between about 0.25% and about 1.80% (w/w), or about 0.75% (w/w), of a polysorbate. For example, the aqueous suspensions of the disclosure can comprise about 0.1, 0.2, 0.3, 0.4, 0.5, 0.6, 0.7, 0.75, 0.8, 0.9, 1, 1.1, 1.2, 1.3, 1.4, 1.5, 1.6, 1.7, 1.8, 1.9, or about 2% (w/w) of the polysorbate. Polysorbates are known in the art as a class of compounds derived from ethoxylated sorbitan esterified with fatty acids. In some embodiments, the polysorbate can be polysorbate 20, polysorbate 40, polysorbate 60, polysorbate 80, or a combination thereof.

In certain embodiments of the invention, the aqueous suspensions can comprise between about 1% and about 10% (w/w), between about 0.5% and about 8% (w/w), or about 5% (w/w) of a polyalkylene glycol. For example, the aqueous suspensions can comprise about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5 or about 10% (w/w) of the polyalkylene glycol. Polyalkylene glycols are known in the art. Preferred polyalkylene glycols include polyethylene glycols. Polyethylene glycols useful in the disclosure will have a molecular weight of between about 300 g/mol and about 10,000 g/mol, including but not limited to PEG 200, PEG 300, PEG 400, PEG 540, PEG 600, PEG 1000, PEG 1450, PEG 1540, PEG 3350, PEG 3500, PEG 4000, PEG 6000, PEG 8000, or a combination thereof.

In certain embodiments of the invention, the aqueous suspensions of the disclosure can comprise between about 0.1% and about 5% (w/w), between about 0.5% and about 4% (w/w), or about 2.5% (w/w) of a $C_{1-12}$alkylene glycol. For example, the aqueous suspensions can comprise about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or about 5% (w/w) of the $C_{1-12}$alkylene glycol. As used herein, a "$C_{1-12}$alkylene glycol" refers to an aliphatic glycol having 1, 2, 3, 4, 5, 6, 7, 8, 9, 10, 11, or 12 carbon atoms. Exemplary $C_{1-2}$alkylene glycols include, for example, propylene glycol and ethylene glycol. In some embodiments of the invention, the $C_{1-12}$alkylene glycol is propylene glycol.

In certain embodiments of the invention, the aqueous suspensions of the disclosure comprise between about 0.1% and about 5% (w/w), between about 0.1% and about 2% (w/w), or about 0.3% (w/w) of a phosphatidylcholine. For example, the aqueous suspensions can comprise about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or about 5% (w/w) of the phosphatidylcholine. Phosphatidylcholines are known in the art as a class of phospholipids that include a choline headgroup. In some embodiments of the invention, the phosphatidylcholine is lecithin.

In certain embodiments of the invention, the aqueous suspensions can comprise one or more additional pharmaceutically acceptable excipients. As used herein, a pharmaceutically acceptable excipient is generally chemically and/or physically compatible with other ingredients in an aqueous suspension, and/or is generally physiologically compatible with the subject recipient thereof. In some embodiments, the one or more additional pharmaceutically acceptable excipients are selected from the group consisting of preservatives, antioxidants, anti-foaming agents or mixtures thereof. In yet further embodiments of the invention, the additional pharmaceutically acceptable excipient is a preservative such as, but not limited to, phenol, cresol, p-hydroxybenzoic ester, chlorobutanol, or mixtures thereof. In yet further embodiments of the invention, the additional pharmaceutically acceptable excipient is an antioxidant such as, but not limited to, ascorbic acid, sodium pyrosulfite, palmitic acid, butylated hydroxyanisole, butylated hydroxytoluene, tocopherols, or mixtures thereof. In yet further embodiments of the invention, the additional pharmaceutically acceptable excipient is an anti-foaming agent such as, but not limited to, dimethicone, simethicone, or mixtures thereof.

In some embodiments of the invention, the aqueous suspensions can comprise a water-soluble excipient that is an aryl-$C_{1-6}$alk-OH, a $C_{1-6}$alkyl-OH, a polysorbate, or a buffering salt, or a combination thereof. In certain embodiments of the invention, the water soluble excipient is an aryl-$C_{1-6}$alk-OH (e.g., benzyl alcohol), a $C_{1-6}$alkyl-OH (e.g., ethanol), and a polysorbate. In further embodiments of the invention, the water-soluble excipient is a $C_{1-6}$alkyl-OH (e.g., ethanol) and a polysorbate. In yet further embodiments of the invention, the water-soluble excipient is an aryl-$C_{1-6}$alk-OH (e.g., benzyl alcohol). In other embodiments of the invention, the water-soluble excipient is an aryl-$C_{1-6}$alk-OH (e.g., benzyl alcohol) and a polysorbate. In some embodiments of the invention, the water-soluble excipient is an aryl-$C_{1-6}$alk-OH (e.g., benzyl alcohol), a polysorbate, and one or more buffering salts. In some embodiments of the invention, the water-soluble excipient is a $C_{1-6}$alkyl-OH (e.g., ethanol), a polysorbate, and one or more buffering salts.

In certain embodiments of the invention, the aqueous suspensions comprise about 100 mg/mL fulvestrant, about 0.5% (w/w) polysorbate 80, about 5.0% (w/w) mannitol, about 0.16% (w/w) PLASDONE™ C-12, about 1.2% (w/w) benzyl alcohol, about 0.75% (w/w) polysorbate 20, and 5 mM of buffering salts.

In certain embodiments of the invention, the aqueous suspensions comprise fulvestrant (about) 100 mg/mL, polysorbate 80 (about 0.5% (w/w)), mannitol (about 5.0% (w/w)), PLASDONE™ C-12 (about 0.16% (w/w)), ethanol (about 4% (w/w)), and polysorbate 20 (about 0.75% (w/w)).

In certain embodiments of the invention, the aqueous suspensions comprise fulvestrant (about 100 mg/mL), polysorbate 80 (about 0.5% (w/w)), mannitol (about 5.0% (w/w)), PLASDONE™ C-12 (about 0.16% (w/w)), ethanol (about 2% (w/w)), polysorbate 20 (about 0.25% (w/w)), and 5 mM of buffering salts.

In certain embodiments of the invention, the aqueous suspensions comprise fulvestrant (about 100 mg/mL), polysorbate 80 (about 0.5% (w/w)), mannitol (about 5.0% (w/w)), PLASDONE™ C-12 (about 0.16% (w/w)), benzyl alcohol (about 2% (w/w)), polysorbate 20 (about 1.5% (w/w)), and 10 mM of buffering salts. In further embodiments of the invention, the buffering salts comprise potassium phosphate monobasic ($KH_2PO_4$)) (about 0.24% (w/w)).

In certain embodiments of the invention, the aqueous suspensions comprise fulvestrant (about 100 mg/mL), polysorbate 80 (about 0.5% (w/w)), mannitol (about 5.0% (w/w)), PLASDONE™ C-12 (about 0.16% (w/w)), benzyl alcohol (about 1.2% (w/w)), polysorbate 20 (about 0.75% (w/w)), and 15 mM of buffering salts. In further embodiments of the invention, the buffering salts comprise potassium phosphate monobasic ($KH_2PO_4$)) (about 0.36% (w/w)).

In certain embodiments of the invention, the aqueous suspensions comprise fulvestrant (about 100 mg/mL), polysorbate 80 (about 0.5% (w/w)), mannitol (about 5.0% (w/w)), PLASDONE™ C-12 (about 0.16% (w/w)), benzyl alcohol (about 2% (w/w)), polysorbate 20 (about 1.5% (w/w)), and 10 mM of buffering salts. In further embodiments of the invention, the buffering salts comprise potassium phosphate monobasic ($KH_2PO_4$)) (about 0.24% (w/w)).

In certain embodiments of the invention, the aqueous suspensions comprise fulvestrant (about 100 mg/mL), polysorbate 80 (about 0.5% (w/w)), mannitol (about 5.0% (w/w)), PLASDONE™ C-12 (about 0.16% (w/w)), benzyl alcohol (about 1.6% (w/w)), polysorbate 20 (about 1.2% (w/w)), and 5 mM of buffering salts. In further embodiments of the invention, the buffering salts comprise potassium phosphate monobasic ($KH_2PO_4$)) (about 0.12% (w/w)). In further embodiments of the invention, the aqueous suspensions can further comprise sodium chloride (about 0.9% (w/w)).

In certain embodiments of the invention, the aqueous suspensions comprise fulvestrant (about 100 mg/mL), polysorbate 80 (about 0.5% (w/w)), mannitol (about 5.0% (w/w)), PLASDONE™ C-12 (about 0.16% (w/w)), benzyl alcohol (about 1.2% (w/w)), polysorbate 20 (about 1.5% (w/w)), and 5 mM of buffering salts. In further embodiments of the invention, the buffering salts comprise potassium phosphate monobasic ($KH_2PO_4$)) (about 0.12% (w/w)).

In certain embodiments of the invention, the aqueous suspensions have a pH of from about 3-10, for example, about 3, 4, 5, 6, 7, 8, 9, or about 10. According to the disclosure, pH is mentioned using conventional instrumentation at ambient temperature, e.g., between 20° C. and 25° C., preferably 23° C. In further embodiments of the invention, the aqueous suspension has a pH of from about 5-8. In further embodiments of the invention, the aqueous suspension has a pH of from about 6-8. In further embodiments of the invention, the aqueous suspension has a pH of from about 3-7. In certain embodiments of the invention, the aqueous suspension has a pH of about 6.0 to 8.0. In particular embodiments of the invention, the aqueous suspension has a pH of about 6.0 to 7.0, 6.5 to 7.0, 6.5 to 7.5, 6.7 to 7.2, 7.0 to 7.2, 7.0 to 7.5, or 7.0 to 8.0. In further embodiments of the invention, the aqueous suspension has a pH of about 7.0.

Methods of Forming Aqueous Suspensions

In some embodiments of the invention, methods of forming an aqueous suspension comprise mixing an aqueous medium and at least one of a surfactant, a polyvinylpyrrolidone, a sugar alcohol, and a water-soluble excipient to form a suspension vehicle, adding an amount of fulvestrant to the suspension vehicle, and dispersing the fulvestrant in the suspension vehicle to form the aqueous suspension. In further embodiments, these methods can comprise homogenizing the aqueous suspension. In yet further embodiments, the methods with or without the homogenizing step can further comprise concentrating the aqueous suspension by phase separating the aqueous suspension and removing a portion of the supernatant. In particular further embodiments, after the concentrating step the methods can further comprise adding one or more surfactants, polyvinylpyrrolidones, sugar alcohols, and water-soluble excipients to the homogenized aqueous fulvestrant suspension and mixing the one or more surfactants, polyvinylpyrrolidones, sugar alcohols, and water-soluble excipients into the suspension. In some embodiments of the invention, the methods comprise a dispersing step performed using high shear mixing, a homogenizing step performed using high pressure homogenization, or both a dispersing step performed using high shear mixing and a homogenizing step performed using high pressure homogenization.

In further embodiments of the invention that include one or more surfactants, polyvinylpyrrolidones, sugar alcohols, and water-soluble excipients, the one or more surfactants, polyvinylpyrrolidones, sugar alcohols, and water-soluble excipients may be incorporated into the formulations at one or more stages of the methods of forming the aqueous suspensions. In some embodiments, at least a portion or all of the surfactants, polyvinylpyrrolidones, sugar alcohols, and water-soluble excipients of an aqueous suspension are added to an aqueous medium along with an amount of fulvestrant prior to some or all of any mixing, homogenization, or supernatant-removal steps. In still other embodiments, at least a portion or all of the one or more surfactants, polyvinylpyrrolidones, sugar alcohols, and water-soluble excipients of an aqueous suspension are added to the aqueous suspensions after some or all of any mixing, homogenization, or supernatant-removal steps have been completed. In further embodiments, at least a portion or all of the surfactants, polyvinylpyrrolidones, and water-soluble excipients of the aqueous suspensions are combined with the aqueous medium and fulvestrant prior to some or all of any mixing, homogenization, or supernatant-removal steps and at least a portion or all of the sugar alcohols and water-soluble excipients are added to the aqueous suspension after some or all of any mixing, homogenization, or supernatant-removal steps.

The fulvestrant particles described herein can be prepared in a method comprising the steps of dispersing fulvestrant particles in a liquid suspension medium and applying mechanical means in the presence of grinding media to reduce the size of the non-solubilized fulvestrant particles to the desired size.

In further embodiments of the invention, one or more solvents, such as water or an alcohol or a combination thereof, present in an aqueous suspension can be removed partially or completely by appropriate techniques known to the art, such as lyophilization or spray drying, to form a dried pharmaceutical composition. In certain embodiments of the invention, a dried pharmaceutical composition can comprise up to about 1%, about 2%, about 5%, or about 10% of the one or more solvents. Dried pharmaceutical compositions formed by lyophilization may be in the form of a lyophilized cake.

In certain embodiments of the invention, aqueous suspensions can be formed by reconstituting a dried pharmaceutical composition (e.g., lyophilized cake). Reconstitution can be performed with an appropriate diluent. In some embodiments, the diluent can be water for injection (WFI). In further embodiments, the diluent can be WFI with sodium chloride in an amount between about 0.01% and about 1.8% w/w, such as, but not limited to, normal saline with 0.9% w/w sodium chloride. In some embodiments of the invention, at least a portion of the excipients other than fulvestrant can be omitted from the aqueous suspension and incorporated as part of the diluent and introduced into the aqueous suspension upon reconstitution of a dried pharmaceutical composition by the diluent to arrive at the final formulation. In further embodiments, the diluent can be WFI and one or more of the water-soluble excipients described elsewhere herein. In yet further embodiments, the diluent can be WFI, one or more of the water-soluble excipients described elsewhere herein, and one or more of the surfactants, the polyvinylpyrrolidones, and the sugar alcohols described elsewhere herein. In further embodiments, aqueous suspensions can be prepared with higher or lower concentrations of constituent components than desired in aqueous suspensions for administration, formed into dried pharmaceutical compositions and placed into vials in appropriate amounts of dried pharmaceutical compositions to achieve target dose amounts of fulvestrant per vial for later reconstitution with an appropriate diluent to form the desired aqueous suspension for administration.

Pharmacokinetics

In certain embodiments of the invention, the aqueous suspensions are bioequivalent to the commercial pharmaceutical composition, FASLODEX®. The single dose PK parameters in postmenopausal advanced breast cancer patients administered FASLODEX® dosed intramuscularly with 500 mg with an additional dose at day 15 are reported as, in geometric mean and coefficient of variation (%), Cmax 25.1 (35.3) ng/mL, Cmin 16.3 (25.9) ng/mL, and AUC 11,400 (33.4) ng-hr/mL.

In further embodiments of the invention, the 90% confidence intervals (CI) of the relative mean $C_{max}$, $AUC_{(0-t)}$ and $AUC_{(0-\infty)}$ of the aqueous suspension of the invention is within 80% to 125% of the relative mean $C_{max}$, $AUC_{(0-t)}$ and $AUC_{(0-\infty)}$, respectively, of FASLODEX®. In yet further embodiments of the invention, the 90% confidence intervals (CI) of the relative mean $C_{max}$, $AUC_{(0-t)}$ and $AUC_{(0-\infty)}$ of the aqueous suspension of the invention is within 80% to 125% of the relative mean $C_{max}$, $AUC_{(0-t)}$ and $AUC_{(0-\infty)}$, respectively, of FASLODEX® in the fasting state. In still further embodiments of the invention, the 90% confidence intervals (CI) of the relative mean $C_{max}$, $AUC_{(0-t)}$ and $AUC_{(0-\infty)}$ of the aqueous suspension of the invention is within 80% to 125% of the relative mean $C_{max}$, $AUC_{(0-t)}$ and $AUC_{(0-\infty)}$, respectively, of FASLODEX® in the fed state.

In other embodiments of the invention, the 90% confidence intervals (CI) of the relative mean $C_{max}$, $AUC_{(0-t)}$ and $AUC_{(0-\infty)}$ of the aqueous suspension of the invention having a fulvestrant concentration of 100 mg/mL is within 80% to 125% of the relative mean $C_{max}$, $AUC_{(0-t)}$ and $AUC_{(0-\infty)}$, respectively, of FASLODEX®. In still other embodiments of the invention, the 90% confidence intervals (CI) of the relative mean $C_{max}$, $AUC_{(0-t)}$ and $AUC_{(0-\infty)}$ of the aqueous suspension of the invention having a fulvestrant concentration of 100 mg/mL is within 80% to 125% of the relative mean $C_{max}$, $AUC_{(0-t)}$ and $AUC_{(0-\infty)}$, respectively, of FASLODEX® in the fasting state. In yet other embodiments of the invention, the 90% confidence intervals (CI) of the relative mean $C_{max}$, $AUC_{(0-t)}$ and $AUC_{(0-\infty)}$ of the aqueous suspension of the invention having a fulvestrant concentration of 100 mg/mL is within 80% to 125% of the relative mean $C_{max}$, $AUC_{(0-t)}$ and $AUC_{(0-\infty)}$, respectively, of FASLODEX® in the fed state.

In particular embodiments of the invention, the aqueous suspension has the single dose and multiple dose pharmacokinetic parameters shown in Tables 1 and 2. Table 1 shows pharmacokinetic parameters for 500 mg dosage of aqueous suspensions of the disclosure. For the data labeled "Single Dose" in Table 1, the fulvestrant blood plasma concentration data are shown for a 500 mg initial dose with an additional 500 mg dose given on day 15. For the data labeled "Multiple Dose Steady State" in Table 1, the fulvestrant blood plasma concentration data are shown for measurement at month 3, after a 500 mg dosage on days 1, 15, 20, and once monthly thereafter. Table 2 shows pharmacokinetic parameters for a single 250 mg dosage of aqueous suspensions of the disclosure. In Table 2, data are expressed as geometric mean (CV %), except for $T_{max}$, which is shown as a median value with a range indicated in parentheses.

TABLE 1

|  | $C_{max}$ (ng/mL) | $C_{min}$ (ng/mL) | AUC (ng · hr/mL) |
|---|---|---|---|
| Single Dose | 20.08-31.375 | 13.04-20.375 | 9,120-14,250 |
| Multiple Dose Steady State | 22.4-35.0 | 9.76-15.25 | 10,480-16,375 |

TABLE 2

|  | I | II | III | IV | V | VI | VII |
|---|---|---|---|---|---|---|---|
| $C_{max}$ (µg/L) | 8.20 (63.8) | 4.76 (68.1) | 8.2 | 4-8.5 | 11.8 (6.6) | 8.3 (8.8) | 8-12 |
| $C_{min}$ (µg/L) | 2.62 (33.4) | 2.38 (47.7) | 2.6 | 2.0-3.0 |  |  |  |
| $T_{max}$ (days) | 6.97 (1.86-7.95) | 8.8 (6.97-12.0) | 7 | 6-9 | 4.2 (8.3) | 4.6 (11.2) | 4-5 |
| $AUC_{28}$ (µg · day/L) | 148 (45.3) | 88.4 (47.3) | 148 | 80-150 | 369 (4.1) | 333 (3.0) | 325-375 |

In particular embodiments, a dose of about 500 mg of fulvestrant in an aqueous suspension of the invention is bioequivalent to 500 mg of the commercial pharmaceutical composition, FASLODEX®. In certain embodiments, a dose of less than 500 mg of fulvestrant in an aqueous suspension of the invention is bioequivalent to 500 mg of the commercial pharmaceutical composition, FASLODEX®. In further embodiments, a dose of about 400 to 450 mg of fulvestrant in an aqueous suspension of the invention is bioequivalent to 500 mg of the commercial pharmaceutical composition, FASLODEX®. In still further embodiments, a dose of about 350 to 400 mg of fulvestrant in an aqueous suspension of the invention is bioequivalent to 500 mg of the commercial pharmaceutical composition, FASLODEX®. In yet further embodiments, a dose of about 300 to 350 mg of fulvestrant in an aqueous suspension of the invention is bioequivalent to 500 mg of the commercial pharmaceutical composition, FASLODEX®. In even further embodiments, a dose of about 250 to 300 mg of fulvestrant in an aqueous suspension of the invention is bioequivalent to 500 mg of the commercial pharmaceutical composition, FASLODEX®.

In other embodiments of the invention, a 500 mg dose of fulvestrant in an aqueous suspension of the invention provides 90% confidence intervals (CI) of the relative mean $C_{max}$, $AUC_{(0-t)}$ and $AUC_{(0-\infty)}$ within 80% to 125% of the relative mean $C_{max}$, $AUC_{(0-t)}$ and $AUC_{(0-\infty)}$, respectively, of a 500 mg dose of FASLODEX®.

In other embodiments of the invention, a dose of less than 500 mg of fulvestrant in an aqueous suspension of the invention provides 90% confidence intervals (CI) of the relative mean $C_{max}$, $AUC_{(0-t)}$ and $AUC_{(0-\infty)}$ within 80% to 125% of the relative mean $C_{max}$, $AUC_{(0-t)}$ and $AUC_{(0-\infty)}$, respectively, of a 500 mg dose of FASLODEX®.

In some embodiments of the invention, aqueous suspensions of the invention can be administered as a single intramuscular injection, with the 90% confidence intervals (CI) of the relative mean Cmax, AUC(0-t) and AUC(0-∞) of fulvestrant within 80% to 125% of the relative mean Cmax, AUC(0-t) and AUC(0-∞), respectively, of fulvestrant after administration of 500 mg of fulvestrant in the form of FASLODEX® administered intramuscularly as two 5 mL injections. In further embodiments, such aqueous suspensions administered as a single intramuscular injection comprise a dose of about 500 mg of fulvestrant. In yet further embodiments, such aqueous suspensions administered as a single intramuscular injection comprise a dose of about 500 mg of fulvestrant in an injection volume of between about 3.0 mL to about 6.0 mL, between about 3.0 mL to about 5.0 mL, between about 4.5 mL to about 5.5 mL, between about 3.5 mL to about 4.5 mL, about 3.0 mL, about 3.5 mL, about 4.0 mL, about 4.5 mL, or about 5.0 mL. In some embodiments of the invention, aqueous suspensions of the invention can be administered as a single subcutaneous injection, with the 90% confidence intervals (CI) of the relative mean Cmax, AUC(0-t) and AUC(0-∞) of fulvestrant within 80% to 125% of the relative mean Cmax, AUC(0-t) and AUC(0-∞), respectively, of fulvestrant after administration of 500 mg of fulvestrant in the form of FASLODEX® administered intramuscularly as two 5 mL injections. In further embodiments, such aqueous suspensions administered as a single subcutaneous injection comprise a dose of about 500 mg of fulvestrant. In yet further embodiments, such aqueous suspensions administered as a single subcutaneous injection comprise a dose of about 500 mg of fulvestrant in an injection volume of between about 3.0 mL to about 6.0 mL between about 3.0 mL to about 5.0 mL, between about 4.5 mL to about 5.5 mL, between about 3.5 mL to about 4.5 mL, about 3.0 mL, about 3.5 mL, about 4.0 mL, about 4.5 mL, or about 5.0 mL.

In certain embodiments of the invention, the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80% of the relative mean Cmax of FASLODEX®. It is believed that such embodiments may provide benefits by providing a therapeutically effect amount of fulvestrant exposure to a subject while reducing the degree of one or more Cmax-driven side-effects or toxicities in comparison to the degree of side-effects or toxicities experienced by a subject from receiving a therapeutically effective amount of fulvestrant exposure from one or more dosages of FASLODEX®.

In some embodiments of the invention, the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80%, less than 75%, less than 70%, less than 65%, less than 60%, less than 55%, less than 50%, less than 45%, or less than 40% of the relative mean Cmax of FASLODEX®. In further embodiments, such aqueous suspensions are administered as a single intramuscular injection and comprise a dose of about 500 mg of fulvestrant at a concentration of between about 80 mg/mL and about 170 mg/mL or about 100 mg/mL.

In yet further embodiments of the invention, the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80%, less than 75%, less than 70%, less than 65%, less than 60%, less than 55%, less than 50%, less than 45%, or less than 40% of the relative mean $C_{max}$ of FASLODEX® in the fasting state. In further embodiments, such aqueous suspensions are administered as a single intramuscular injection and comprise a dose of about 500 mg of fulvestrant at a concentration of between about 80 mg/mL and about 170 mg/mL or about 100 mg/mL.

In still further embodiments of the invention, the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80%, less than 75%, less than 70%, less than 65%, less than 60%, less than 55%, less than 50%, less than 45%, or less than 40% of the relative mean Cmax of FASLODEX® in the fed state. In further embodiments, such aqueous suspensions are administered as a single intramuscular injection and comprise a dose of about 500 mg of fulvestrant at a concentration of between about 80 mg/mL and about 170 mg/mL or about 100 mg/mL.

In some embodiments of the invention, the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean $C_{max}$ of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX®. In further embodiments, such aqueous suspensions are administered as a single intramuscular injection and comprise a dose of about 500 mg of fulvestrant at a concentration of between about 80 mg/mL and about 170 mg/mL or about 100 mg/mL. In further embodiments, such aqueous suspensions are administered as a single subcutaneous injection and comprise a dose of about 500 mg of fulvestrant at a concentration of between about 80 mg/mL and about 170 mg/mL or about 100 mg/mL.

In yet further embodiments of the invention, the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, the relative mean Cmax of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX® in the fasting state. In further embodiments, such aqueous suspensions are administered as a single intramuscular injection and comprise a dose of about 500 mg of fulvestrant at a concentration of between about 80 mg/mL and about 170 mg/mL or about 100 mg/mL. In further embodiments, such aqueous suspensions are administered as a single subcutaneous injection and comprise a dose of about 500 mg of fulvestrant at a concentration of between about 80 mg/mL and about 170 mg/mL or about 100 mg/mL.

In still further embodiments of the invention, the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX® in the fed state. In further embodiments, such aqueous suspensions are administered as a single intramuscular injection and comprise a dose of about 500 mg of fulvestrant at a concentration of between about 80 mg/mL and about 170 mg/mL or about 100 mg/mL. In further embodiments, such aqueous suspensions are administered as a single subcutaneous injection and comprise a dose of about 500 mg of fulvestrant at a concentration of between about 80 mg/mL and about 170 mg/mL or about 100 mg/mL.

In particular embodiments, a dose of greater than 500 mg of fulvestrant in an aqueous suspension of the invention, for example, up to about 3000 mg, is bioequivalent to 500 mg of the commercial pharmaceutical composition, FASLODEX®. In some embodiments, a dose of about 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant in an aqueous suspension of the invention is bioequivalent to 500 mg of the commercial pharmaceutical composition, FASLODEX®. In further embodiments, a dose of about 500 to 1000 mg of fulvestrant in an aqueous suspension of the invention is bioequivalent to 500 mg of the commercial pharmaceutical composition, FASLODEX®. In still further embodiments, a dose of about 1000 to 2000 mg of fulvestrant in an aqueous suspension of the invention is bioequivalent to 500 mg of the commercial pharmaceutical composition, FASLODEX®. In yet further embodiments, a dose of about 2000 to 3000 mg of fulvestrant in an aqueous suspension of the invention is bioequivalent to 500 mg of the commercial pharmaceutical composition, FASLODEX®. In even further embodiments, a dose of about 750 to 1000 mg of fulvestrant in an aqueous suspension of the invention is bioequivalent to 500 mg of the commercial pharmaceutical composition, FASLODEX®.

In other embodiments of the invention, a dose of greater than 500 mg of fulvestrant in an aqueous suspension of the invention, for example, up to about 3000 mg, provides 90% confidence intervals (CI) of the relative mean $C_{max}$, $AUC_{(0-t)}$ and $AUC_{(0-\infty)}$ within 80% to 125% of the relative mean $C_{max}$, $AUC_{(0-t)}$ and $AUC_{(0-\infty)}$, respectively, of a 500 mg dose of FASLODEX®. For example, a dose of about 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant in an aqueous suspension of the invention provides 90% confidence intervals (CI) of the relative mean $C_{max}$, $AUC_{(0-t)}$ and $AUC_{(0-\infty)}$ within 80% to 125% of the relative mean $C_{max}$, $AUC_{(0-t)}$ and $AUC_{(0-\infty)}$, respectively, of a 500 mg dose of FASLODEX®.

In some embodiments of the invention, aqueous suspensions of the invention comprising greater than 500 mg of fulvestrant, for example, up to about 3000 mg, can be administered as a single intramuscular injection, with the 90% confidence intervals (CI) of the relative mean Cmax, $AUC_{(0-t)}$ and AUC(0-∞) of fulvestrant within 80% to 125% of the relative mean Cmax, AUC(0-t) and AUC(0-∞), respectively, of fulvestrant after administration of 500 mg of fulvestrant in the form of FASLODEX® administered intramuscularly as two 5 mL injections. For example, aqueous suspensions of the invention comprising about 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant can be administered as a single intramuscular injection, with the 90% confidence intervals (CI) of the relative mean Cmax, AUC(0-t) and AUC(0-∞) of fulvestrant within 80% to 125% of the relative mean Cmax, AUC(0-t) and AUC(0-∞), respectively, of fulvestrant after administration of 500 mg of fulvestrant in the form of FASLODEX® administered intramuscularly as two 5 mL injections.

In yet further embodiments, such aqueous suspensions administered as a single intramuscular injection comprise a dose of greater than 500 mg of fulvestrant, for example, up to about 3000 mg of fulvestrant, in an injection volume of between about 3.0 mL to about 6.0 mL, between about 3.0 mL to about 5.0 mL, between about 4.5 mL to about 5.5 mL, between about 3.5 mL to about 4.5 mL, about 3.0 mL, about 3.5 mL, about 4.0 mL, about 4.5 mL, or about 5.0 mL. For example, aqueous suspensions of the invention administered as a single intramuscular injection comprise about 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant in an injection volume of between about 3.0 mL to about 6.0 mL, between about 3.0 mL to about 5.0 mL, between about 4.5 mL to about 5.5 mL, between about 3.5 mL to about 4.5 mL, about 3.0 mL, about 3.5 mL, about 4.0 mL, about 4.5 mL, or about 5.0 mL.

In some embodiments of the invention, aqueous suspensions of the invention comprising greater than 500 mg of fulvestrant, for example, up to about 3000 mg, can be administered as a single subcutaneous injection, with the 90% confidence intervals (CI) of the relative mean Cmax, AUC(0-t) and AUC(0-∞) of fulvestrant within 80% to 125% of the relative mean Cmax, AUC(0-t) and AUC(0-∞), respectively, of fulvestrant after administration of 500 mg of fulvestrant in the form of FASLODEX® administered intramuscularly as two 5 mL injections. In further embodiments, such aqueous suspensions administered as a single subcutaneous injection comprise a dose of 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant. In yet further embodiments, such aqueous suspensions administered as a single subcutaneous injection comprise a dose of greater than 500 mg of fulvestrant, for example, up to about 3000 mg, in an injection volume of between about 3.0 mL to about 6.0 mL, between about 3.0 mL to about 5.0 mL, between about 4.5 mL to about 5.5 mL, between about 3.5 mL to about 4.5 mL, about 3.0 mL, about 3.5 mL, about 4.0 mL, about 4.5 mL, or about 5.0 mL.

In some embodiments of the invention, aqueous suspensions are administered as a single intramuscular injection and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL, and the 90% confidence intervals (CI) of the relative mean $AUC_{(0-t)}$, relative mean $AUC_{(0-\infty)}$, or both, of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80%, less than 75%, less than 70%, less than 65%, less than 60%, less than 55%, less than 50%, less than 45%, or less than 40% of the relative mean Cmax of FASLODEX®.

In yet further embodiments of the invention, aqueous suspensions are administered as a single intramuscular injection and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80%, less than 75%, less than 70%, less than 65%, less than 60%, less than 55%, less than 50%, less than 45%, or less than 40% of the relative mean Cmax of FASLODEX® in the fasting state.

In still further embodiments of the invention, aqueous suspensions are administered as a single intramuscular injection and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80%, less than 75%, less than 70%, less than 65%, less than 60%, less than 55%, less than 50%, less than 45%, or less than 40% of the relative mean Cmax of FASLODEX® in the fed state.

In some embodiments of the invention, aqueous suspensions are administered as a single intramuscular injection and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean $C_{max}$ of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX®.

In yet further embodiments of the invention, aqueous suspensions are administered as a single intramuscular injection and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, the relative mean Cmax of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX® in the fasting state.

In still further embodiments of the invention, aqueous suspensions are administered as a single intramuscular injection and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX® in the fed state.

In some embodiments of the invention, aqueous suspensions of the invention comprising greater than 500 mg of fulvestrant, for example, up to about 3000 mg, can be administered as two intramuscular injections, with the 90% confidence intervals (CI) of the relative mean Cmax, AUC (0-t) and AUC(0-∞) of fulvestrant within 80% to 125% of the relative mean Cmax, AUC(0-t) and AUC(0-∞), respectively, of fulvestrant after administration of 500 mg of fulvestrant in the form of FASLODEX® administered intramuscularly as two 5 mL injections. For example, aqueous suspensions of the invention comprising about 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant can be administered as two intramuscular injections, with the 90% confidence intervals (CI) of the relative mean Cmax, AUC(0-t) and AUC(0-∞) of fulvestrant within 80% to 125% of the relative mean Cmax, AUC(0-t) and AUC(0-∞), respectively, of fulvestrant after administration of 500 mg of fulvestrant in the form of FASLODEX® administered intramuscularly as two 5 mL injections.

In yet further embodiments, such aqueous suspensions administered as two intramuscular injections comprise a dose of greater than 500 mg of fulvestrant, for example, up to about 3000 mg of fulvestrant, in an injection volume for each injection of between about 3.0 mL to about 6.0 mL, between about 3.0 mL to about 5.0 mL, between about 4.5 mL to about 5.5 mL, between about 3.5 mL to about 4.5 mL, about 3.0 mL, about 3.5 mL, about 4.0 mL, about 4.5 mL, or about 5.0 mL. For example, aqueous suspensions of the invention administered as two intramuscular injections comprise about 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant in an injection volume for each injection of between about 3.0 mL to about 6.0 mL, between about 3.0 mL to about 5.0 mL, between about 4.5 mL to about 5.5 mL, between about 3.5 mL to about 4.5 mL, about 3.0 mL, about 3.5 mL, about 4.0 mL, about 4.5 mL, or about 5.0 mL.

In some embodiments of the invention, aqueous suspensions of the invention comprising greater than 500 mg of fulvestrant, for example, up to about 3000 mg, can be administered as two subcutaneous injections, with the 90% confidence intervals (CI) of the relative mean Cmax, AUC (0-t) and AUC(0-∞) of fulvestrant within 80% to 125% of the relative mean Cmax, AUC(0-t) and AUC(0-∞), respectively, of fulvestrant after administration of 500 mg of fulvestrant in the form of FASLODEX® administered intramuscularly as two 5 mL injections. In further embodiments, such aqueous suspensions administered as two subcutaneous injections comprise a dose of 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant. In yet further embodiments, such aqueous suspensions administered as two subcutaneous injections comprise a dose of greater than 500 mg of fulvestrant, for example, up to about 3000 mg, in an injection volume for each injection of between about 3.0 mL to about 6.0 mL, between about 3.0 mL to about 5.0 mL, between about 4.5 mL to about 5.5 mL, between about 3.5 mL to about 4.5 mL, about 3.0 mL, about 3.5 mL, about 4.0 mL, about 4.5 mL, or about 5.0 mL.

In some embodiments of the invention, aqueous suspensions are administered as two intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL, and the 90% confidence intervals (CI) of the relative mean $AUC_{(0-t)}$, relative mean $AUC_{(0-\infty)}$, or both, of aqueous suspensions of the invention is within 80% to 125% of the relative mean $AUC_{(0-t)}$ and relative mean $AUC_{(0-\infty)}$, respectively, of FASLODEX®, and the relative mean $C_{max}$ of aqueous suspensions of the invention is less than 80%, less than 75%, less than 70%, less than 65%, less than 60%, less than 55%, less than 50%, less than 45%, or less than 40% of the relative mean Cmax of FASLODEX®.

In yet further embodiments of the invention, aqueous suspensions are administered as two intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80%, less than 75%, less than 70%, less than 65%, less than 60%, less than 55%, less than 50%, less than 45%, or less than 40% of the relative mean Cmax of FASLODEX® in the fasting state.

In still further embodiments of the invention, aqueous suspensions are administered as two intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80%, less than 75%, less than 70%, less than 65%, less than 60%, less than 55%, less than 50%, less than 45%, or less than 40% of the relative mean Cmax of FASLODEX® in the fed state.

In some embodiments of the invention, aqueous suspensions are administered as two intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean $C_{max}$ of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX®.

In yet further embodiments of the invention, aqueous suspensions are administered as two intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, the relative mean Cmax of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX® in the fasting state.

In still further embodiments of the invention, aqueous suspensions are administered as two intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX® in the fed state.

In some embodiments of the invention, aqueous suspensions of the invention comprising greater than 500 mg of fulvestrant, for example, up to about 3000 mg, can be administered as three or more intramuscular injections, with the 90% confidence intervals (CI) of the relative mean Cmax, AUC(0-t) and AUC(0-∞) of fulvestrant within 80% to 125% of the relative mean Cmax, AUC(0-t) and AUC(0-∞), respectively, of fulvestrant after administration of 500 mg of fulvestrant in the form of FASLODEX® administered intramuscularly as two 5 mL injections. For example, aqueous suspensions of the invention comprising about 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant can be administered as three or more intramuscular injections, with the 90% confidence intervals (CI) of the relative mean Cmax, AUC(0-t) and AUC(0-∞) of fulvestrant within 80% to 125% of the relative mean Cmax, AUC(0-t) and AUC(0-∞), respectively, of fulvestrant after administration of 500 mg of fulvestrant in the form of FASLODEX® administered intramuscularly as two 5 mL injections.

In yet further embodiments, such aqueous suspensions administered as three or more intramuscular injections comprise a dose of greater than 500 mg of fulvestrant, for example, up to about 3000 mg of fulvestrant, in an injection volume for each injection of between about 3.0 mL to about 6.0 mL, between about 3.0 mL to about 5.0 mL, between about 4.5 mL to about 5.5 mL, between about 3.5 mL to about 4.5 mL, about 3.0 mL, about 3.5 mL, about 4.0 mL, about 4.5 mL, or about 5.0 mL. For example, aqueous suspensions of the invention administered as three or more intramuscular injections comprise about 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant in an injection volume for each injection of between about 3.0 mL to about 6.0 mL, between about 3.0 mL to about 5.0 mL, between about 4.5 mL to about 5.5 mL, between about 3.5 mL to about 4.5 mL, about 3.0 mL, about 3.5 mL, about 4.0 mL, about 4.5 mL, or about 5.0 mL.

In some embodiments of the invention, aqueous suspensions of the invention comprising greater than 500 mg of fulvestrant, for example, up to about 3000 mg, can be administered as three or more subcutaneous injections, with the 90% confidence intervals (CI) of the relative mean Cmax, AUC(0-t) and AUC(0-∞) of fulvestrant within 80% to 125% of the relative mean Cmax, AUC(0-t) and AUC(0-∞), respectively, of fulvestrant after administration of 500 mg of fulvestrant in the form of FASLODEX® administered intramuscularly as two 5 mL injections. In further embodiments, such aqueous suspensions administered as three or more subcutaneous injections comprise a dose of 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant. In yet further embodiments, such aqueous suspensions administered as three or more subcutaneous injections comprise a dose of greater than 500 mg of fulvestrant, for example, up to about 3000 mg, in an injection volume for each injection of between about 3.0 mL to about 6.0 mL, between about 3.0 mL to about 5.0 mL, between about 4.5 mL to about 5.5 mL, between about 3.5 mL to about 4.5 mL, about 3.0 mL, about 3.5 mL, about 4.0 mL, about 4.5 mL, or about 5.0 mL.

In some embodiments of the invention, aqueous suspensions are administered as three or more intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL, and the 90% confidence intervals (CI) of the relative mean $AUC_{(0-t)}$, relative mean $AUC_{(0-\infty)}$, or both, of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80%, less than 75%, less than 70%, less than 65%, less than 60%, less than 55%, less than 50%, less than 45%, or less than 40% of the relative mean Cmax of FASLODEX®.

In yet further embodiments of the invention, aqueous suspensions are administered as three or more intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80%, less than 75%, less than 70%, less than 65%, less than 60%, less than 55%, less than 50%, less than 45%, or less than 40% of the relative mean Cmax of FASLODEX® in the fasting state.

In still further embodiments of the invention, aqueous suspensions are administered as three or more intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is less than 80%, less than 75%, less than 70%, less than 65%, less than 60%, less than 55%, less than 50%, less than 45%, or less than 40% of the relative mean Cmax of FASLODEX® in the fed state.

In some embodiments of the invention, aqueous suspensions are administered as three or more intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX®.

In yet further embodiments of the invention, aqueous suspensions are administered as three or more intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, the relative mean $C_{max}$ of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX® in the fasting state.

In still further embodiments of the invention, aqueous suspensions are administered as three or more intramuscular injections and comprise a dose of greater than 500 mg of fulvestrant, for example, up to about 3000 mg (e.g., 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, or about 3000 mg of fulvestrant), at a concentration of between about 80 mg/mL and about 170 mg/mL or about 100 mg/mL and the 90% confidence intervals (CI) of the relative mean $AUC_{(0-t)}$, relative mean $AUC_{(0-\infty)}$, or both of aqueous suspensions of the invention is within 80% to 125% of the relative mean $AUC_{(0-t)}$ and relative mean $AUC_{(0-\infty)}$, respectively, of FASLODEX®, and the relative mean Cmax of aqueous suspensions of the invention is about 45%, about 50%, about 55%, about 60%, about 65%, about 70%, about 75%, about 80%, about 85%, about 90%, within about 45% to about 55%, within about 55% to about 65%, within about 65% to about 75%, within about 50% to about 60%, within about 60% to about 70%, or within about 70% to about 80% of the relative mean Cmax of FASLODEX® in the fed state.

Methods of Treatment

In further embodiments, the invention is directed to methods of treatment comprising administration of a pharmaceutically effective amount of any of the aqueous suspensions described herein to a patient in need thereof. In particular embodiments, the invention is directed to a method of treating breast cancer, comprising administering a pharmaceutically acceptable amount of any of the aqueous suspensions described herein. In certain embodiments, the breast cancer is metastatic breast cancer. In other embodiments of the invention, the breast cancer is hormone receptor (HR)-positive breast cancer. In still other embodiments of the invention, the invention is directed to a method of treating hormone receptor (HR)-positive breast cancer in a post-menopausal woman comprising administration of a pharmaceutically effective amount of any of the aqueous suspensions described herein. In yet other embodiments, the invention is directed to a method of treating hormone receptor (HR)-positive breast cancer in a post-menopausal woman with disease progression following antiestrogen therapy comprising administration of a pharmaceutically effective amount of any of the aqueous suspensions described herein. In yet further embodiments, the invention is directed to a method of treating HR-positive, human epidermal growth factor receptor 2 (HER2)-negative advanced or metastatic breast cancer in a woman with disease progression after endocrine therapy. In even yet further embodiments, the invention is directed to methods of treatment comprising administration via intramuscular injection to the ventrogluteal site or the dorsogluteal site. In other embodiments, the invention is directed to methods of treatment comprising administration of the aqueous suspensions described herein via subcutaneous injection.

In particular embodiments of the invention, an aqueous suspension as described herein is administered on days 1, 15, 29, and once monthly thereafter. In further embodiments of the invention, a 500 mg dose of any of the aqueous suspensions as described herein is administered on days 1, 15, 29, and once monthly thereafter. In still further embodiments of the invention, a 250 mg dose of any of the aqueous suspensions as described herein is administered on days 1, 15, 29, and once monthly thereafter.

In certain embodiments of the invention, an aqueous suspension as described herein is administered as a single injection. In other embodiments of the invention, a 500 mg dose of any of the aqueous suspensions as described herein is administered as a single injection. In yet other embodiments of the invention, a 500 mg dose of any of the aqueous suspensions as described herein is administered as a single 5 mL injection. In further embodiments of the invention, a 500 mg dose of any of the aqueous suspensions as described herein is administered as a single 4 mL injection. In yet further embodiments, a 500 mg dose of any of the aqueous suspensions as described herein is administered as a single 3 mL injection.

In other embodiments of the invention, a total dose of an amount of fulvestrant greater than 500 mg, for example, up to about 3000 mg, of any of the aqueous suspensions as described herein is administered. For example, a total dose of an amount of fulvestrant that is about 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2800, 2900, or about 3000 mg, as any aqueous suspension as described herein is administered. In some embodiments of the invention, an aqueous suspension as described herein is administered as a single injection. In other embodiments of the invention, a dose of an amount of fulvestrant greater than 500 mg, for example, up to about 3000 mg, of any of the aqueous suspensions as described herein is administered, as a single injection. In yet other embodiments of the invention, a dose of an amount of fulvestrant greater than 500 mg, for example, up to about 3000 mg, of any of the aqueous suspensions as described herein is administered as a single 5 mL injection. In further embodiments of the invention, a 500 mg dose, for example, up to about 3000 mg, of any of the aqueous suspensions as described herein is administered as a single 4 mL injection. In yet further embodiments, a dose of an amount of fulvestrant greater than 500 mg, for example, up to about 3000 mg, of any of the aqueous suspensions as described herein is administered as a single 3 mL injection. In yet further embodiments, a dose of an amount of fulvestrant greater than 500 mg, for example, up to about 3000 mg, of any of the aqueous suspensions as described herein is administered as a single 6 mL injection. In yet further embodiments, a dose of an amount of fulvestrant greater than 500 mg, for example, up to about 3000 mg, of any of the aqueous suspensions as described herein is administered as a single injection of about 5.5 mL, about 6.0 mL, about 6.5 mL, about 7.0 mL, or about 7.5 mL.

In particular embodiments of the invention, an aqueous suspension as described herein is administered as two injections. In further embodiments of the invention, a 500 mg dose of any of the aqueous suspensions as described herein is administered as two injections. In still further embodiments of the invention, a 500 mg dose of any of the aqueous suspensions as described herein is administered as two 5 mL injections. In yet further embodiments of the invention, a 500 mg dose of any of the aqueous suspensions as described herein is administered as two 1.5 mL injections, two 2 mL injections, two 2.5 mL injections, two 3 mL injections, two 3.5 mL injections, or two 4 mL injections.

In further embodiments of the invention, a dose of an amount of fulvestrant greater than 500 mg, for example, up to about 3000 mg, of any of the aqueous suspensions as described herein is administered as two injections. For example, a total dose of an amount of fulvestrant that is about 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2800, 2900, or about 3000 mg, as any aqueous suspension as described herein in administered in two injections. In still further embodiments of the invention, a dose of an amount of fulvestrant greater than 500 mg for example, up to about 3000 mg, of any of the aqueous suspensions as described herein is administered as two injections of about 4.5 mL, about 5.0 mL, about 5.5 mL, about 6.0 mL, about 6.5 mL, about 7.0 mL, or about 7.5 mL. In still further embodiments of the invention, a dose of an amount of fulvestrant greater than 500 mg, for example, up to about 3000 mg, of any of the aqueous suspensions as described herein is administered as two 5 mL injections. In yet further embodiments of the invention, a dose of an amount of fulvestrant greater than 500 mg for example, up to about 3000 mg, of any of the aqueous suspensions as described herein is administered as two 1.5 mL injections, two 2 mL injections, two 2.5 mL injections, two 3 mL injections, two 3.5 mL injections, or two 4 mL injections.

In certain embodiments of the invention, an aqueous suspension is administered as two injections of doses about 500 mg fulvestrant in each injection for a total dose of about 1000 mg. In some embodiments, the two injections of doses of about 500 mg fulvestrant in each are each about 5.0 mL.

In certain embodiments of the invention, an aqueous suspension is administered as two injections of doses about 550 mg fulvestrant in each injection for a total dose of about 1100 mg. In certain embodiments of the invention, an aqueous suspension is administered as two injections of doses about 600 mg fulvestrant in each injection for a total dose of about 1200 mg. In certain embodiments of the invention, an aqueous suspension is administered as two injections of doses about 650 mg fulvestrant in each injection for a total dose of about 1300 mg. In certain embodiments of the invention, an aqueous suspension is administered as two injections of doses about 700 mg fulvestrant in each injection for a total dose of about 1400 mg. In certain embodiments of the invention, an aqueous suspension is administered as two injections of doses about 750 mg fulvestrant in each injection for a total dose of about 1500 mg. In certain embodiments of the invention, an aqueous suspension is administered as two injections of doses about 800 mg fulvestrant in each injection for a total dose of about 1600 mg. In certain embodiments of the invention, an aqueous suspension is administered as two injections of doses about 850 mg fulvestrant in each injection for a total dose of about 1700 mg. In certain embodiments of the invention, an aqueous suspension is administered as two injections of doses about 900 mg fulvestrant in each injection for a total dose of about 1800 mg. In certain embodiments of the invention, an aqueous suspension is administered as two injections of doses about 950 mg fulvestrant in each injection for a total dose of about 1900 mg. In certain embodiments of the invention, an aqueous suspension is administered as two injections of doses about 1000 mg fulvestrant in each injection for a total dose of about 2000 mg. In certain embodiments of the invention, an aqueous suspension is administered as two injections of doses about 1100 mg fulvestrant in each injection for a total dose of about 2200 mg. In certain embodiments of the invention, an aqueous suspension is administered as two injections of doses about 1200 mg fulvestrant in each injection for a total dose of about 2400 mg. In certain embodiments of the invention, an aqueous suspension is administered as two injections of doses about 1300 mg fulvestrant in each injection for a total dose of about 2600 mg. In certain embodiments of the invention, an aqueous suspension is administered as two injections of doses about 1400 mg fulvestrant in each injection for a total dose of about 2800 mg. In certain embodiments of the invention, an aqueous suspension is administered as two injections of doses about 1500 mg fulvestrant in each injection for a total dose of about 3000 mg.

In particular embodiments of the invention, an aqueous suspension as described herein is administered as three or more injections. In further embodiments of the invention, a 500 mg dose of any of the aqueous suspensions as described herein is administered as three or more injections. In still further embodiments of the invention, a 500 mg dose of any of the aqueous suspensions as described herein is administered as three or more 5 mL injections. In yet further embodiments of the invention, a 500 mg dose of any of the aqueous suspensions as described herein is administered as three or more 1.5 mL injections, three or more 2 mL injections, three or more 2.5 mL injections, three or more 3 mL injections, three or more 3.5 mL injections, or three or more 4 mL injections.

In further embodiments of the invention, a dose of an amount of fulvestrant greater than 500 mg, for example, up to about 3000 mg, of any of the aqueous suspensions as described herein is administered as three or more injections having an equal amount of fulvestrant in each injection. For example, a total dose of an amount of fulvestrant that is about 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2800, 2900, or about 3000 mg, as any aqueous suspension as described herein is administered in three or more injections. In still further embodiments of the invention, a dose of an amount of fulvestrant greater than 500 mg for example, up to about 3000 mg, of any of the aqueous suspensions as described herein is administered as three or more injections of about 4.5 mL, about 5.0 mL, about 5.5 mL, about 6.0 mL, about 6.5 mL, about 7.0 mL, or about 7.5 mL. In still further embodiments of the invention, a dose of an amount of fulvestrant greater than 500 mg, for example, up to about 3000 mg, of any of the aqueous suspensions as described herein is administered as three or more 5 mL injections. In yet further embodiments of the invention, a dose of an amount of fulvestrant greater than 500 mg for example, up to about 3000 mg, of any of the aqueous suspensions as described herein is administered as three or more 1.5 mL injections, three or more 2 mL injections, three or more 2.5 mL injections, three or more 3 mL injections, three or more 3.5 mL injections, or three or more 4 mL injections.

In certain embodiments of the invention, an aqueous suspension is administered as three or more injections of equal amounts of fulvestrant in each injection for a total dose of about 1000 mg. In some embodiments, the two injections of doses of about 500 mg fulvestrant in each are each about 5.0 mL. In certain embodiments of the invention, an aqueous suspension is administered as three or more injections of equal amounts of fulvestrant in each injection for a total dose of about 1100 mg. In certain embodiments of the invention, an aqueous suspension is administered as three or more injections of equal amounts of fulvestrant in each injection for a total dose of about 1200 mg. In certain embodiments of the invention, an aqueous suspension is administered as three or more injections of equal amounts of fulvestrant in each injection for a total dose of about 1300 mg. In certain embodiments of the invention, an aqueous suspension is administered as three or more injections of equal amounts of fulvestrant in each injection for a total dose of about 1400 mg. In certain embodiments of the invention, an aqueous suspension is administered as three or more injections of equal amounts of fulvestrant in each injection for a total dose of about 1500 mg. In certain embodiments of the invention, an aqueous suspension is administered as three or more injections of equal amounts of fulvestrant in each injection for a total dose of about 1600 mg. In certain embodiments of the invention, an aqueous suspension is administered as three or more injections of equal amounts of fulvestrant in each injection for a total dose of about 1700 mg. In certain embodiments of the invention, an aqueous suspension is administered as three or more injections of equal amounts of fulvestrant in each injection for a total dose of about 1800 mg. In certain embodiments of the invention, an aqueous suspension is administered as three or more injections of equal amounts of fulvestrant in each injection for a total dose of about 1900 mg. In certain embodiments of the invention, an aqueous suspension is administered as three or more injections of equal amounts of fulvestrant in each injection for a total dose of about 2000 mg. In certain embodiments of the invention, an aqueous suspension is administered as three or more injections of equal amounts of fulvestrant in each injection for a total dose of about 2200 mg. In certain embodiments of the invention, an aqueous suspension is administered as three or more injections of equal amounts of fulvestrant in each injection for a total dose of about 2400 mg. In certain embodiments of the invention, an aqueous suspension is administered as three or more injections of equal amounts of fulvestrant in each injection for a total dose of about 2600 mg. In certain embodiments of the invention, an aqueous suspension is administered as three or more injections of equal amounts of fulvestrant in each injection for a total dose of about 2800 mg. In certain embodiments of the invention, an aqueous suspension is administered as three or more injections of equal amounts of fulvestrant in each injection for a total dose of about 3000 mg.

The aqueous suspensions described herein may be administered alone, or in combination with one or more additional therapeutic agents as defined herein. An additional therapeutic agent may be used to treat one or more core symptoms and/or comorbidities associated with cancer in general or breast cancer in particular. In one aspect, fulvestrant is formulated (and administered) with at least one therapeutic agent as a fixed dose. In another aspect, fulvestrant is formulated (and administered) separately from the therapeutic agent(s).

Some examples of therapeutic agents that may be used in combination with the aqueous suspensions include, but are not limited to, e.g., a EGFR kinase inhibitor, a PDGFR kinase inhibitor, a FGFR kinase inhibitor, or any of the other cytotoxic, chemotherapeutic, antihormonal, anti-angiogenic, antiproliferative, pro-apoptotic, anti-HER2, radiation or a radiopharmaceutical, signal transduction inhibitors, or other anti-cancer agents or treatments. Examples of particular agents that can be used in combination with the aqueous suspensions of the disclosure include palbociclib, letrozole, anastrozole, doxorubicin, paclitaxel, docetaxel, vinorelbine, and 5-fluorouracil. In other embodiments, therapeutic agents that may be used in combination with aqueous suspensions include, but are not limited to, agents or treatments for one or more of pain, nausea, emesis, hot flushes, constipation, and dizziness.

Methods of Dose Administration

In certain embodiments of the invention, aqueous suspensions as described herein can be administered in multiple doses. In some embodiments of the invention, a first dose with a first-dose fulvestrant amount can be administered on day 1. In further embodiments of the invention, a second dose with a second-dose fulvestrant amount can be administered after a first time period subsequent to the first dose. In yet further embodiments of the invention, one or more additional doses with a third-dose fulvestrant amount can be administered after a second time period subsequent to the second dose and repeated at a frequency of one dose per a third time period. In some embodiments of the invention, the administration in multiple doses described herein can be used in the methods of treating breast cancer of the invention.

In some embodiments of the invention, the first-dose fulvestrant amount can be about between about 500 mg and about 3000 mg, between about 500 mg and about 1500 mg, between about 750 mg and about 1500 mg, between about 750 mg and about 1250 mg, between about 750 mg and about 1000 mg, between about 800 mg and about 1200 mg, between about 850 mg and about 1150 mg, between about 900 mg and about 1100 mg, or between about 950 mg and about 1050 mg. In further embodiments of the invention, the first-dose fulvestrant amount can be about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, about 2700 mg, about 2750 mg, about 2800 mg, about 2850 mg, about 2900 mg, about 2950 mg, or about 3000 mg.

In some embodiments of the invention, the second-dose fulvestrant amount can be between about 500 mg and about 3000 mg, between about 500 mg and about 1500 mg, between about 750 mg and about 1500 mg, between about 750 mg and about 1250 mg, between about 750 mg and about 1000 mg, between about 800 mg and about 1200 mg, between about 850 mg and about 1150 mg, between about 900 mg and about 1100 mg, or between about 950 mg and about 1050 mg. In further embodiments of the invention, the second-dose fulvestrant amount can be about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, about 2700 mg, about 2750 mg, about 2800 mg, about 2850 mg, about 2900 mg, about 2950 mg, or about 3000 mg.

In some embodiments of the invention, the third-dose fulvestrant amount can be between about 500 mg and about 3000 mg, between about 500 mg and about 1500 mg, between about 750 mg and about 1500 mg, between about 750 mg and about 1250 mg, between about 750 mg and about 1000 mg, between about 800 mg and about 1200 mg, between about 850 mg and about 1150 mg, between about 900 mg and about 1100 mg, or between about 950 mg and about 1050 mg. In further embodiments of the invention, the third-dose fulvestrant amount can be about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, about 2700 mg, about 2750 mg, about 2800 mg, about 2850 mg, about 2900 mg, about 2950 mg, or about 3000 mg.

In certain embodiments of the invention, the first time period subsequent to the first dose when the second dose can be administered can be between about 1 day and about 30 days, between about 5 days and about 25 days, between about 10 days and about 20 days, between about 10 days and about 15 days, between about 12 days and about 16 days, or between about 13 days and about 15 days. In certain embodiments of the invention, the first time period subsequent to the first dose when the second dose can be administered can be about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days.

In certain embodiments of the invention, the second time period subsequent to the second dose when the first of the one or more additional doses can be administered can be between about 1 day and about 30 days, between about 5 days and about 25 days, between about 10 days and about 20 days, between about 10 days and about 15 days, between about 12 days and about 16 days, or between about 13 days and about 15 days. In further embodiments of the invention, the second time period subsequent to the second dose when the first of the one or more additional doses can be administered can be about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days.

In some embodiments of the invention, the one or more additional doses can be repeatedly administered at a frequency of one dose per a third time period that can be between about 1 days and about 180 days, between about 1 days and about 150 days, between about 1 days and about 120 days, between about 1 days and about 90 days, between about 60 days and about 90 days, between about 75 days and about 90 days, between about 30 days and about 60 days, between about 45 days and about 60 days, between about 45 days and about 75 days, between about 50 days and about 70 days, between about 55 days and about 65 days, between about 10 days and about 50 days, between about 15 days and about 45 days, between about 20 days and about 40 days, between about 25 days and about 35 days, between about 5 days and about 35 days, between about 10 days and about 30 days, between about 15 days and about 25 days, between about 1 weeks and about 12 weeks, between about 6 weeks and about 12 weeks, between about 7 weeks and about 12 weeks, between about 8 weeks and about 12 weeks, between about 9 weeks and about 12 weeks, between about 10 weeks and about 12 weeks, between about 11 weeks and about 12 weeks, between about 4 weeks and about 10 weeks, between about 5 weeks and about 10 weeks, between about 6 weeks and about 10 weeks, between about 7 weeks and about 10 weeks, between about 8 weeks and about 10 weeks, between about 9 weeks and about 10 weeks, between about 2 weeks and about 8 weeks, between about 3 weeks and about 8 weeks, between about 4 weeks and about 8 weeks, between about 5 weeks and about 8 weeks, between about 6 weeks and about 8 weeks, between about 7 weeks and about 8 weeks, between about 1 weeks and about 6 weeks, between about 2 weeks and about 6 weeks, between about 3 weeks and about 6 weeks, between about 4 weeks and about 6 weeks, between about 5 weeks and about 6 weeks, between about 1 weeks and about 4 weeks, between about 2 weeks and about 4 weeks, between about 3 weeks and about 4 weeks, between about 1 weeks and about 3 weeks, between about 2 weeks and about 3 weeks, between about 1 months and about 3 months, between about 2 months and about 3 months, between about 1.5 months and 2.5 months, between about 1.5 months and 3.5 months, between about 2.0 months and about 3.5 months, or between about 2.0 months and about 2.5 months. In further embodiments of the invention, the one or more additional doses can be repeatedly administered at a frequency of one dose per a third time period that can be about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, about 50 days, about 51 days, about 52 days, about 53 days, about 54 days, about 55 days, about 56 days, about 57 days, about 58 days, about 59 days, about 60 days, about 61 days, about 62 days, about 63 days, about 64 days, about 65 days, about 66 days, about 67 days, about 68 days, about 69 days, about 70 days, about 71 days, about 72 days, about 73 days, about 74 days, about 75 days, about 76 days, about 77 days, about 78 days, about 79 days, about 80 days, about 81 days, about 82 days, about 83 days, about 84 days, about 85 days, about 86 days, about 87 days, about 88 days, about 89 days, about 90 days, about 1 month, about 1.5 months, about 2 months, about 2.5 months, about 3 months, or about 3.5 months.

In some embodiments of the invention, a first dose with a first-dose fulvestrant amount can be administered on day 1. In further embodiments of the invention, a second dose with a second-dose fulvestrant amount can be administered after a first time period subsequent to the first dose. In yet further embodiments of the invention, one or more additional doses with a third-dose fulvestrant amount can be administered after a second time period subsequent to the second dose and repeated at a frequency of one dose per a third time period.

In some embodiments of the invention, a first dose with a first-dose fulvestrant amount of about 550 mg can be administered on day 1, a second dose with a second-dose fulvestrant amount of about 550 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 600 mg can be administered on day 1, a second dose with a second-dose fulvestrant amount of about 600 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 650 mg can be administered on day 1, a second dose with a second-dose fulvestrant amount of about 650 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 700 mg can be administered on day 1, a second dose with a second-dose fulvestrant amount of about 700 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 750 mg can be administered on day 1, a second dose with a second-dose fulvestrant amount of about 750 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 800 mg can be administered on day 1, a second dose with a second-dose fulvestrant amount of about 800 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 850 mg can be administered on day 1, a second dose with a second-dose fulvestrant amount of about 850 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 900 mg can be administered on day 1, a second dose with a second-dose fulvestrant amount of about 900 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 950 mg can be administered on day 1, a second dose with a second-dose fulvestrant amount of about 950 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 1000 mg can be administered on day 1, a second dose with a second-dose fulvestrant amount of about 1000 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 1050 mg can be administered on day 1, a second dose with a second-dose fulvestrant amount of about 1050 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 1100 mg can be administered on day 1, a second dose with a second-dose fulvestrant amount of about 1100 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 1150 mg can be administered on day 1, a second dose with a second-dose fulvestrant amount of about 1150 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 1200 mg can be administered on day 1, a second dose with a second-dose fulvestrant amount of about 1200 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 1250 mg can be administered on day 1, a second dose with a second-dose fulvestrant amount of about 1250 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 2 months.

In some embodiments of the invention, a first dose with a first-dose fulvestrant amount of about 550 mg can be administered on day 1, a second dose with a second-dose fulvestrant amount of about 550 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 months.

In some embodiments of the invention, a first dose with a first-dose fulvestrant amount of about 600 mg can be administered on day 1, a second dose with a second-dose fulvestrant amount of about 600 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 months.

In some embodiments of the invention, a first dose with a first-dose fulvestrant amount of about 650 mg can be administered on day 1, a second dose with a second-dose fulvestrant amount of about 650 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 months.

In some embodiments of the invention, a first dose with a first-dose fulvestrant amount of about 700 mg can be administered on day 1, a second dose with a second-dose fulvestrant amount of about 700 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 months.

In some embodiments of the invention, a first dose with a first-dose fulvestrant amount of about 750 mg can be administered on day 1, a second dose with a second-dose fulvestrant amount of about 750 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 month.

In some embodiments of the invention, a first dose with a first-dose fulvestrant amount of about 800 mg can be administered on day 1, a second dose with a second-dose fulvestrant amount of about 800 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 month.

In some embodiments of the invention, a first dose with a first-dose fulvestrant amount of about 850 mg can be administered on day 1, a second dose with a second-dose fulvestrant amount of about 850 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 month.

In some embodiments of the invention, a first dose with a first-dose fulvestrant amount of about 900 mg can be administered on day 1, a second dose with a second-dose fulvestrant amount of about 900 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 month.

In some embodiments of the invention, a first dose with a first-dose fulvestrant amount of about 950 mg can be administered on day 1, a second dose with a second-dose fulvestrant amount of about 950 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 month.

In some embodiments of the invention, a first dose with a first-dose fulvestrant amount of about 1000 mg can be administered on day 1, a second dose with a second-dose fulvestrant amount of about 1000 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 month.

In some embodiments of the invention, a first dose with a first-dose fulvestrant amount of about 1050 mg can be administered on day 1, a second dose with a second-dose fulvestrant amount of about 1050 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 month.

In some embodiments of the invention, a first dose with a first-dose fulvestrant amount of about 1100 mg can be administered on day 1, a second dose with a second-dose fulvestrant amount of about 1100 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 month.

In some embodiments of the invention, a first dose with a first-dose fulvestrant amount of about 1150 mg can be administered on day 1, a second dose with a second-dose fulvestrant amount of about 1150 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 month.

In some embodiments of the invention, a first dose with a first-dose fulvestrant amount of about 1200 mg can be administered on day 1, a second dose with a second-dose fulvestrant amount of about 1200 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 month.

In some embodiments of the invention, a first dose with a first-dose fulvestrant amount of about 1250 mg can be administered on day 1, a second dose with a second-dose fulvestrant amount of about 1250 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 1 month.

In some embodiments of the invention, a first dose with a first-dose fulvestrant amount of about 550 mg can be administered on day 1, a second dose with a second-dose fulvestrant amount of about 550 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 600 mg can be administered on day 1, a second dose with a second-dose fulvestrant amount of about 600 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 650 mg can be administered on day 1, a second dose with a second-dose fulvestrant amount of about 650 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 700 mg can be administered on day 1, a second dose with a second-dose fulvestrant amount of about 700 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 750 mg can be administered on day 1, a second dose with a second-dose fulvestrant amount of about 750 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 800 mg can be administered on day 1, a second dose with a second-dose fulvestrant amount of about 800 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 850 mg can be administered on day 1, a second dose with a second-dose fulvestrant amount of about 850 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 900 mg can be administered on day 1, a second dose with a second-dose fulvestrant amount of about 900 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 950 mg can be administered on day 1, a second dose with a second-dose fulvestrant amount of about 950 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 1000 mg can be administered on day 1, a second dose with a second-dose fulvestrant amount of about 1000 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 1050 mg can be administered on day 1, a second dose with a second-dose fulvestrant amount of about 1050 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 1100 mg can be administered on day 1, a second dose with a second-dose fulvestrant amount of about 1100 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 1150 mg can be administered on day 1, a second dose with a second-dose fulvestrant amount of about 1150 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 1200 mg can be administered on day 1, a second dose with a second-dose fulvestrant amount of about 1200 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 1250 mg can be administered on day 1, a second dose with a second-dose fulvestrant amount of about 1250 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 4 weeks.

In some embodiments of the invention, a first dose with a first-dose fulvestrant amount of about 550 mg can be administered on day 1, a second dose with a second-dose fulvestrant amount of about 550 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 600 mg can be administered on day 1, a second dose with a second-dose fulvestrant amount of about 600 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 650 mg can be administered on day 1, a second dose with a second-dose fulvestrant amount of about 650 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 700 mg can be administered on day 1, a second dose with a second-dose fulvestrant amount of about 700 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 750 mg can be administered on day 1, a second dose with a second-dose fulvestrant amount of about 750 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 800 mg can be administered on day 1, a second dose with a second-dose fulvestrant amount of about 800 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 850 mg can be administered on day 1, a second dose with a second-dose fulvestrant amount of about 850 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 900 mg can be administered on day 1, a second dose with a second-dose fulvestrant amount of about 900 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 950 mg can be administered on day 1, a second dose with a second-dose fulvestrant amount of about 950 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 1000 mg can be administered on day 1, a second dose with a second-dose fulvestrant amount of about 1000 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 1050 mg can be administered on day 1, a second dose with a second-dose fulvestrant amount of about 1050 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 1100 mg can be administered on day 1, a second dose with a second-dose fulvestrant amount of about 1100 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 1150 mg can be administered on day 1, a second dose with a second-dose fulvestrant amount of about 1150 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 1200 mg can be administered on day 1, a second dose with a second-dose fulvestrant amount of about 1200 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 1250 mg can be administered on day 1, a second dose with a second-dose fulvestrant amount of about 1250 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 6 weeks.

In some embodiments of the invention, a first dose with a first-dose fulvestrant amount of about 550 mg can be administered on day 1, a second dose with a second-dose fulvestrant amount of about 550 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 600 mg can be administered on day 1, a second dose with a second-dose fulvestrant amount of about 600 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 650 mg can be administered on day 1, a second dose with a second-dose fulvestrant amount of about 650 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 700 mg can be administered on day 1, a second dose with a second-dose fulvestrant amount of about 700 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 750 mg can be administered on day 1, a second dose with a second-dose fulvestrant amount of about 750 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 800 mg can be administered on day 1, a second dose with a second-dose fulvestrant amount of about 800 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 850 mg can be administered on day 1, a second dose with a second-dose fulvestrant amount of about 850 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 900 mg can be administered on day 1, a second dose with a second-dose fulvestrant amount of about 900 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 950 mg can be administered on day 1, a second dose with a second-dose fulvestrant amount of about 950 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 1000 mg can be administered on day 1, a second dose with a second-dose fulvestrant amount of about 1000 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 1050 mg can be administered on day 1, a second dose with a second-dose fulvestrant amount of about 1050 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 1100 mg can be administered on day 1, a second dose with a second-dose fulvestrant amount of about 1100 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 1150 mg can be administered on day 1, a second dose with a second-dose fulvestrant amount of about 1150 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 1200 mg can be administered on day 1, a second dose with a second-dose fulvestrant amount of about 1200 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

In some embodiments of the invention, a first dose with a first-dose fulvestrant amount of about 1250 mg can be administered on day 1, a second dose with a second-dose fulvestrant amount of about 1250 mg can be administered after a first time period of about 14 days subsequent to the first dose, and one or more additional doses with a third-dose fulvestrant amount of about 500 mg can be administered after a second time period of about 14 days subsequent to the second dose and repeated at a frequency of one dose per a third time period of about 8 weeks.

Non-Solubilized Fulvestrant Particles

In certain embodiments of the invention, the non-solubilized fulvestrant particles have a diameter, as measured by laser diffraction, greater than or equal to about 1 micron. In yet further embodiments of the invention, at least a portion of the non-solubilized fulvestrant particles have a laser diffraction diameter less than about 1 micron. In other embodiments of the invention the non-solubilized fulvestrant particles have a laser diffraction diameter greater than or equal to about 2 microns. In still other embodiments of the invention, at least a portion of the non-solubilized fulvestrant particles have a laser diffraction diameter less than about 2 microns.

In certain embodiments of the invention, the non-solubilized fulvestrant particles have a laser diffraction diameter greater than or equal to about 0.5 microns. In other embodiments of the invention, at least a portion of the non-solubilized fulvestrant particles have a laser diffraction diameter less than about 0.5 microns. In other embodiments of the invention, the non-solubilized fulvestrant particles have a laser diffraction diameter greater than or equal to about 1 micron. In other embodiments of the invention, at least a portion of the non-solubilized fulvestrant particles have a laser diffraction diameter less than about 1 microns. In still other embodiments of the invention, the non-solubilized fulvestrant particles have a laser diffraction diameter greater than or equal to about 1.5 microns. In other embodiments of the invention, at least a portion of the non-solubilized fulvestrant particles have a laser diffraction diameter less than about 1.5 microns. In yet other embodiments of the invention, the non-solubilized fulvestrant particles have a laser diffraction diameter greater than or equal to about 2 microns. In other embodiments of the invention, at least a portion of the non-solubilized fulvestrant particles have a laser diffraction diameter less than about 2 microns.

In further embodiments of the invention, about 98% of non-solubilized fulvestrant particles have a laser diffraction diameter greater than or equal to about 0.5 microns. In other embodiments of the invention, about 98% of non-solubilized fulvestrant particles have a laser diffraction diameter greater than or equal to about 1 micron. In still other embodiments of the invention, about 98% of non-solubilized fulvestrant particles have a laser diffraction diameter greater than or equal to about 1.5 microns. In yet other embodiments of the invention, about 98% of non-solubilized fulvestrant particles have a laser diffraction diameter greater than or equal to about 2 microns.

In certain embodiments of the invention, the non-solubilized fulvestrant particles have an LD Dv(90) between about 4 microns and about 120 microns, between about 4 microns and about 100 microns, between about 4 microns and about 75 microns, between about 4 microns and about 60 microns, between about 4 microns and about 50 microns, between about 4 microns and about 40 microns, between about 4 microns and about 30 microns, between about 4 microns and about 20 microns, between about 4 microns and about 15 microns, between about 4 microns and about 10 microns, between about 15 microns and about 35 microns, between about 20 microns and about 60 microns, between about 20 microns and about 45 microns, between about 20 microns and about 30 microns, between about 30 microns and about 50 microns, or between about 4 microns and about 9 microns. In other embodiments of the invention, the non-solubilized fulvestrant particles have a LD Dv(90) equal to about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 25 microns, about 30 microns, about 35 microns, about 40 microns, about 45 microns, about 50 microns, about 55 microns, about 60 microns, about 65 microns, about 70 microns, about 75 microns, about 80 microns, about 85 microns, about 90 microns, about 95 microns, about 100 microns, about 105 microns, about 110 microns, about 115 microns, or about 120 microns.

In certain embodiments of the invention, the non-solubilized fulvestrant particles have an LD Dv(90) less than or equal to about 120 microns. In certain embodiments of the invention, the non-solubilized fulvestrant particles have an LD Dv(90) less than or equal to about 100 microns. In certain embodiments of the invention, the non-solubilized fulvestrant particles have an LD Dv(90) less than or equal to about 80 microns. In certain embodiments of the invention, the non-solubilized fulvestrant particles have an LD Dv(90) less than or equal to about 60 microns. In certain embodiments of the invention, the non-solubilized fulvestrant particles have an LD Dv(90) less than or equal to about 50 microns. In certain embodiments of the invention, the non-solubilized fulvestrant particles have an LD Dv(90) less than or equal to about 40 microns. In certain embodiments of the invention, the non-solubilized fulvestrant particles have an LD Dv(90) less than or equal to about 30 microns. In further embodiments of the invention, the particles have an LD Dv(90) less than or equal to about 25 microns. In further embodiments of the invention, the particles have an LD Dv(90) less than or equal to about 18 microns. In further embodiments of the invention, the particles have an LD Dv(90) less than or equal to about 16 microns. In further embodiments of the invention, the particles have an LD Dv(90) less than or equal to about 14 microns. In still further embodiments of the invention, the particles have an LD Dv(90) less than or equal to about 11 microns. In yet further embodiments of the invention, the particles have an LD Dv(90) less than or equal to about 9 microns. In yet further embodiments of the invention, the particles have an LD Dv(90) less than or equal to about 7 microns. In yet further embodiments of the invention, the particles have an LD Dv(90) less than or equal to about 5 microns. In particular embodiments of the invention, particles have an LD Dv(90) between about 9-14 microns. In other embodiments of the invention, the particles have an LD Dv(90) between about 12-14 microns. In yet other embodiments of the invention, the particles have an LD Dv(90) between about 9-11 microns. In yet other embodiments of the invention, the particles have an LD Dv(90) between about 7-9 microns. In yet other embodiments of the invention, the particles have an LD Dv(90) between about 6-8 microns. In yet other embodiments of the invention, the particles have an LD Dv(90) between about 6-7 microns. In yet other embodiments of the invention, the particles have an LD Dv(90) between about 3-6 microns.

In certain embodiments of the invention, the non-solubilized fulvestrant particles have an LD Dv(50) between about 2 microns and about 35 microns, between about 2 microns and about 25 microns, between about 2 microns and about 20 microns, between about 2 microns and about 15 microns, between about 2 microns and about 10 microns, between about 2 microns and about 8 microns, between about 2 microns and about 7 microns, between about 2 microns and about 6 microns, between about 2 microns and about 5 microns, between about 2 microns and about 4 microns, between about 5 microns and about 10 microns, between about 5.5 microns and about 9.0 microns, between about 5 microns and about 15 microns, between about 7 microns and about 10 microns, between about 8 microns and about 10 microns, or between about 9 microns and about 16 microns. In other embodiments of the invention, the non-solubilized fulvestrant particles have a LD Dv(50) equal to about 2 microns, 3 microns, 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 25 microns, about 30 microns, or about 35 microns.

In certain embodiments of the invention, the non-solubilized fulvestrant particles have an LD Dv(50) less than or equal to about 9 microns. In other embodiments of the invention, the particles have an LD Dv(50) less than or equal to about 7 microns. In other embodiments of the invention, the particles have an LD Dv(50) less than or equal to about 6 microns. In yet other embodiments of the invention, the particles have an LD Dv(50) less than or equal to about 5 microns. In particular embodiments of the invention, the particles have an LD Dv(50) less than or equal to about 4 microns. In further embodiments of the invention, the particles have an LD Dv(50) less than or equal to about 3 microns. In further embodiments of the invention, the particles have an LD Dv(50) between about 4-6 microns. In further embodiments of the invention, the particles have an LD Dv(50) between about 3-5 microns. In yet further embodiments of the invention, the particles have an LD Dv(50) between about 3-4 microns. In yet further embodiments of the invention, the particles have an LD Dv(50) between about 2-3 microns.

In certain embodiments of the invention, the non-solubilized fulvestrant particles have an LD Dv(10) no more than about 3 microns, about 2 microns, or about 1 microns. In further embodiments of the invention, the particles have an LD Dv(10) between about 1 micron and about 3 microns. In still further embodiments of the invention, the particles have an LD Dv(10) greater than or equal to about 2 microns. In yet further embodiments of the invention, the particles have an LD Dv(10) between about 1.5 microns to about 2.5 microns. In other embodiments, the particles have an LD Dv(10) between about 1.5 microns and about 2.1 microns. In yet further embodiments of the invention, the particles have an LD Dv(10) between about 1 micron to about 2 microns. In yet further embodiments of the invention, the particles have an LD Dv(10) between about 1.0 micron to about 1.5 microns. In even further embodiments of the invention, the particles have an LD Dv(10) of about 2 microns. In even further embodiments of the invention, the particles have an LD Dv(10) of about 1.5 microns.

In certain embodiments of the invention, the non-solubilized fulvestrant particles have an LD Dv(90) less than or equal to about 25 microns and an LD Dv(50) less than or equal to about 9 microns. In particular embodiments of the invention, the particles have an LD Dv(90) less than or equal to about 16 microns and an LD Dv(50) less than or equal to about 6 microns. In other embodiments of the invention, the particles have an LD Dv(90) less than or equal to about 11 microns and an LD Dv(50) less than or equal to about 5 microns. In yet other embodiments of the invention, the particles have an LD Dv(90) less than or equal to about 9 microns and an LD Dv(50) less than or equal to about 4 microns. In yet other embodiments of the invention, the particles have an LD Dv(90) less than or equal to about 8 microns and an LD Dv(50) less than or equal to about 4 microns.

In certain embodiments of the invention, the non-solubilized fulvestrant particles have an LD Dv(90) between about 9-14 microns and an LD Dv(50) between about 4-6 microns. In still other embodiments of the invention, the particles have an LD Dv(90) between about 9-11 microns and an LD Dv(50) between about 4-6 microns. In particular embodiments of the invention, the particles have an LD Dv(90) between about 12-14 microns and an LD Dv(50) between about 4-6 microns. In further embodiments of the invention, the particles have an LD Dv(90) between about 6-8 microns and an LD Dv(50) between about 2-4 microns. In further embodiments of the invention the non-solubilized fulvestrant particles have a laser diffraction diameter greater than or equal to about 1 micron. In yet further embodiments of the invention, at least a portion of the non-solubilized fulvestrant particles have a laser diffraction diameter less than about 1 micron. In other embodiments of the invention the non-solubilized fulvestrant particles have a laser diffraction diameter greater than or equal to about 2 microns. In still other embodiments of the invention, at least a portion of the non-solubilized fulvestrant particles have a laser diffraction diameter less than about 2 microns.

In certain embodiments of the invention, the non-solubilized fulvestrant particles have an LD Dv(90) between about 9-14 microns, an LD Dv(50) between about 4-6 microns, and an LD Dv(10) between about 2-3 microns. In other embodiments of the invention, the particles have an LD Dv(90) between about 9-11 microns, an LD Dv(50) between about 4-6 microns, and an LD Dv(10) between about 2-3 microns. In yet other embodiments of the invention, the particles have an LD Dv(90) between about 12-14 microns, an LD Dv(50) between about 4-6 microns, and an LD Dv(10) between about 2-3 microns. In yet other embodiments of the invention, the particles have an LD Dv(90) between about 6-9 microns, an LD Dv(50) between about 2-4 microns, and an LD Dv(10) between about 1-2 microns. In further embodiments of the invention the non-solubilized fulvestrant particles have a laser diffraction diameter greater than or equal to about 1 micron. In yet further embodiments of the invention, at least a portion of the non-solubilized fulvestrant particles have a laser diffraction diameter less than about 1 micron. In other embodiments of the invention the non-solubilized fulvestrant particles have a laser diffraction diameter greater than or equal to about 2 microns. In still other embodiments of the invention, at least a portion of the non-solubilized fulvestrant particles have a laser diffraction diameter less than about 2 microns.

In certain embodiments of the invention, the non-solubilized fulvestrant particles have an LD Dv(90) between about 9-14 microns, an LD Dv(50) between about 4-6 microns, and an LD Dv(10) between about 2-3 microns, and the non-solubilized fulvestrant particles have a laser diffraction diameter greater than or equal to about 1 micron. In other embodiments of the invention, the particles have an LD Dv(90) between about 9-14 microns, an LD Dv(50) between about 4-6 microns, and an LD Dv(10) between about 2-3 microns, and at least a portion of the non-solubilized fulvestrant particles have a laser diffraction diameter less than about 1 micron. In yet other embodiments of the invention, the non-solubilized fulvestrant particles have an LD Dv(90) between about 30 microns and about 110 microns, an LD Dv(50) between about 5 microns and about 30 microns, and an LD Dv(10) between about 1.5 microns and about 3 microns. In other embodiments of the invention, the particles have an LD Dv(90) between about 9-14 microns, an LD Dv(50) between about 4-6 microns, and an LD Dv(10) between about 2-3 microns, and the non-solubilized fulvestrant particles have a laser diffraction diameter greater than or equal to about 2 microns. In still other embodiments of the invention, the particles have an LD Dv(90) between about 9-14 microns, an LD Dv(50) between about 4-6 microns, and an LD Dv(10) between about 2-3 microns, and at least a portion of the non-solubilized fulvestrant particles have a laser diffraction diameter less than about 2 microns. In yet other embodiments of the invention, the particles have an LD Dv(90) between about 6-9 microns, an LD Dv(50) between about 2-4 microns, an LD Dv(10) between about 1-2 microns, and the non-solubilized fulvestrant particles have a laser diffraction diameter greater than or equal to about 0.5 microns. In yet other embodiments of the invention, the particles have an LD Dv(90) between about 6-9 microns, an LD Dv(50) between about 2-4 microns, an LD Dv(10) between about 1-2 microns, and at least a portion of the non-solubilized fulvestrant particles have a laser diffraction diameter less than about 0.5 microns. In further embodiments of the invention the non-solubilized fulvestrant particles have a laser diffraction diameter greater than or equal to about 1 micron. In yet further embodiments of the invention, at least a portion of the non-solubilized fulvestrant particles have a laser diffraction diameter less than about 1 micron. In other embodiments of the invention the non-solubilized fulvestrant particles have a laser diffraction diameter greater than or equal to about 2 microns. In still other embodiments of the invention, at least a portion of the non-solubilized fulvestrant particles have a laser diffraction diameter less than about 2 microns.

In certain embodiments of the invention, the non-solubilized fulvestrant particles have an LD Dv(90) between about 15 microns to about 35 microns, an LD Dv(50) between about 5.5 microns to about 9.0 microns, and an LD Dv(10) between about 1.5 microns to about 2.1 microns.

In certain embodiments of the invention, the non-solubilized fulvestrant particles have a sonicated LD Dv(10) between about 0.9 microns and about 1.5 microns, between about 1.0 microns and about 1.2 microns, or between about 1.0 microns and about 1.3 microns. In other embodiments of the invention, the non-solubilized fulvestrant particles have a sonicated LD Dv(10) equal to about 0.9 microns, 1.0 microns, 1.1 microns, about 1.2 microns, about 1.3 microns, about 1.4 microns, or about 1.5 microns.

In certain embodiments of the invention, the non-solubilized fulvestrant particles have a sonicated LD Dv(50) between about 2.5 microns and about 5.0 microns, between about 2.5 microns and about 4.5 microns, between about 2.5 microns and about 3.5 microns, between about 3.0 microns and about 4.0 microns, or between about 3.0 microns and about 3.5 microns. In other embodiments of the invention, the non-solubilized fulvestrant particles have a sonicated LD Dv(50) equal to about 2.5 microns, 2.6 microns, 2.7 microns, about 2.8 microns, about 2.9 microns, about 3.0 microns, about 3.1 microns, about 3.2 microns, about 3.3 microns, about 3.4 microns, about 3.5 microns, about 3.6 microns, about 3.7 microns, about 3.8 microns, about 3.9 microns, about 4.0 microns, about 4.1 microns, about 4.2 microns, about 4.3 microns, about 4.4 microns, about 4.5 microns, or about 5.0 microns.

In certain embodiments of the invention, the non-solubilized fulvestrant particles have a sonicated LD Dv(90) between about 6.0 microns and about 10.0 microns, between about 6.5 microns and about 9.0 microns, between about 6.0 microns and about 9.0 microns, between about 6.5 microns and about 7.5 microns, or between about 6.5 microns and about 8.5 microns. In other embodiments of the invention, the non-solubilized fulvestrant particles have a sonicated LD Dv(90) equal to about 6.0 microns, 6.5 microns, 7.0 microns, about 7.5 microns, about 8.0 microns, about 8.5 microns, about 9.0 microns, about 9.5 microns, or about 10.0 microns. In further embodiments of the invention, the non-solubilized fulvestrant particles have a sonicated LD Dv(90) equal to about 6.1, 6.2, 6.3, 6.4, 6.6, 6.7, 6.8, 6.9, 7.1, 7.2, 7.3, 7.4, 7.6, 7.7, 7.8, 7.9, 8.1, 8.2, 8.3, or about 8.4 microns.

In certain embodiments of the invention, the non-solubilized fulvestrant particles have a sonicated LD Dv(10)

between about 1.0 and about 1.2 microns, a sonicated LD Dv(50) between about 3.0 and about 4.0 microns, and a sonicated LD Dv(90) between about 6 microns and about 9 microns.

In certain embodiments of the invention, the non-solubilized fulvestrant particles have a CE Dv(10) between about 1 microns and about 25 microns, between about 2 microns and about 25 microns, between about 3 microns and about 7 microns, between about 4 microns and about 15 microns, between about 4 microns and about 10 microns, between about 4 microns and about 8 microns, between about 6 microns and about 8 microns, between about 6 microns and about 7 microns, between about 1 microns and about 10 microns, between about 3 microns and about 6 microns, or between about 3.5 microns and about 5.2 microns. In other embodiments of the invention, the non-solubilized fulvestrant particles have a CE Dv(10) equal to about 1 micron, about 2 microns, about 3 microns, about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 21 microns, about 22 microns, about 23 microns, about 24 microns, or about 25 microns.

In certain embodiments of the invention, the non-solubilized fulvestrant particles have a CE Dv(50) between about 5 microns and about 60 microns, between about 5 microns and about 50 microns, between about 9 microns and about 20 microns, between about 9 microns and about 15 microns, between about 10 microns and about 50 microns, between about 10 microns and about 40 microns, between about 10 microns and about 30 microns, between about 10 microns and about 20 microns, between about 15 microns and about 30 microns, between about 15 microns and about 25 microns, between about 15 microns and about 20 microns, between about 10 microns and about 15 microns, between about 8 microns and about 15 microns, between about 7.0 microns and about 16.0 microns, or between about 7.8 microns and about 14.9 microns. In other embodiments of the invention, the non-solubilized fulvestrant particles have a CE Dv(50) equal to about 5 micron, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 21 microns, about 22 microns, about 23 microns, about 24 microns, about 25 microns, about 30 microns, about 35 microns, about 40 microns, about 45 microns, about 50 microns, about 55 microns, or about 60 microns.

In certain embodiments of the invention, the non-solubilized fulvestrant particles have a CE Dv(90) between about 10 microns and about 200 microns, between about 25 microns and about 150 microns, between about 25 microns and about 125 microns, between about 25 microns and about 100 microns, between about 20 microns and about 90 microns, between about 23.3 and about 85.3 microns, between about 25 microns and about 75 microns, between about 25 microns and about 50 microns, between about 25 microns and about 40 microns, between about 25 microns and about 35 microns, between about 35 microns and about 90 microns, between about 35 microns and about 75 microns, between about 35 microns and about 50 microns, between about 35 microns and about 45 microns, between about 50 microns and about 100 microns, between about 50 microns and about 75 microns, or between about 20 microns and about 40 microns. In other embodiments of the invention, the non-solubilized fulvestrant particles have a CE Dv(90) equal to about 10 microns, about 15 microns, about 20 microns, about 25 microns, about 30 microns, about 35 microns, about 40 microns, about 45 microns, about 50 microns, about 55 microns, about 60 microns, about 65 microns, about 70 microns, about 75 microns, about 80 microns, about 85 microns, about 90 microns, about 95 microns, about 100 microns, about 105 microns, about 110 microns, about 115 microns, about 120 microns, about 125 microns, about 130 microns, about 135 microns, about 140 microns, about 145 microns, about 150 microns, about 155 microns, about 160 microns, about 165 microns, about 170 microns, about 175 microns, or about 200 microns.

In certain embodiments of the invention, the non-solubilized fulvestrant particles have a CE Dv(90) between about 35 microns and about 90 microns, a CE Dv(50) between about 10 microns and about 35 microns, and a CE Dv(10) between about 4 microns and about 10 microns. In other embodiments of the invention, the non-solubilized fulvestrant particles have a CE Dv(90) between about 25 microns and about 60 microns, a CE Dv(50) between about 10 microns and about 25 microns, and a CE Dv(10) between about 4 microns and about 8 microns. In other embodiments of the invention, the non-solubilized fulvestrant particles have a CE Dv(90) between about 20 microns and about 35 microns, a CE Dv(50) between about 10 microns and about 20 microns, and a CE Dv(10) between about 4 microns and about 8 microns. In still other embodiments of the invention, the non-solubilized fulvestrant particles have a CE Dv(90) between about 30 microns and about 100 microns, a CE Dv(50) between about 10 microns and about 50 microns, and a CE Dv(10) between about 4 microns and about 10 microns. In yet other embodiments of the invention, the non-solubilized fulvestrant particles have a CE Dv(90) between about 50 microns and about 100 microns, a CE Dv(50) between about 20 microns and about 50 microns, a CE Dv(10) between about 6 microns and about 8 microns. In yet other embodiments of the invention, the non-solubilized fulvestrant particles have a CE Dv(90) between about 50 microns and about 75 microns, a CE Dv(50) between about 30 microns and about 40 microns, a CE Dv(10) between about 8 microns and about 10 microns. In yet other embodiments of the invention, the non-solubilized fulvestrant particles have a CE Dv(90) between about 20 microns and about 60 microns, a CE Dv(50) between about 9 microns and about 20 microns, and a CE Dv(10) between about 3 microns and about 7 microns. In still further embodiments of the invention, the non-solubilized fulvestrant particles have a CE Dv(90) between about 20 microns and about 50 microns, a CE Dv(50) between about 9 microns and about 20 microns, and a CE Dv(10) between about 3 microns and about 7 microns. In other embodiments of the invention, the non-solubilized fulvestrant particles have a CE Dv(90) between about 20 microns and about 45 microns, a CE Dv(50) between about 9 microns and about 20 microns, and a CE Dv(10) between about 3 microns and about 7 microns. In yet further embodiments of the invention, the non-solubilized fulvestrant particles have a CE Dv(90) between about 20 microns and about 40 microns, a CE Dv(50) between about 9 microns and about 15 microns, and a CE Dv(10) between about 3 microns and about 7 microns. In further embodiments of the invention, the non-solubilized fulvestrant particles have a CE Dv(90) between about 20 microns and about 35 microns, a CE Dv(50) between about 9 microns and about 15 microns, and a CE Dv(10) between about 3 microns and about 7 microns. In still other embodiments of the invention, the non-solubilized fulvestrant particles have a CE Dv(90) between about 20 microns and about 45 microns, a CE Dv(50) between about 9 microns and about 15 microns, and a CE Dv(10) between about 3 microns and about 7 microns. In still other embodiments of the invention, the non-solubilized fulvestrant particles have a CE Dv(10) between about 3.0 microns and about 6.0 microns, a CE Dv(50) between about 7.0 microns and about 16.0 microns, and a CE Dv(90) between about 20 microns and about 90 microns. In yet other embodiments of the invention, the non-solubilized fulvestrant particles have a CE Dv(10) between about 3.5 microns and about 5.2 microns, a CE Dv(50) between about 7.8 microns and about 14.9 microns, and a CE Dv(90) between about 23.3 and about 85.3 microns.

In certain embodiments of the invention, the non-solubilized fulvestrant particles have a CE Dn(90) between about 4 microns and about 20 microns, between about 6 microns and about 15 microns, between about 6 microns and about 12 microns, between about 8 microns and about 12 microns, between about 8 microns and about 11 microns, between about 4 microns and about 10 microns, between about 4 microns and about 8 microns, between about 4 microns and about 7 microns, or between about 4 microns and about 6 microns. In other embodiments of the invention, the non-solubilized fulvestrant particles have a CE Dn(90) equal to about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, or about 20 microns.

In certain embodiments of the invention, the non-solubilized fulvestrant particles have a CE Dn(50) between about 2.0 microns and about 10.0 microns, between about 2.0 microns and about 8.0 microns, between about 2.0 microns and about 6.0 microns, between about 2.0 microns and about 5.0 microns, between about 3.0 microns and about 5.0 microns, between about 3.5 microns and about 4.5 microns, between about 2.0 microns and about 4.0 microns, between about 2.5 microns and about 4.5 microns, or between about 2.5 microns and about 3.5 microns. In other embodiments of the invention, the non-solubilized fulvestrant particles have a CE Dn(50) equal to about 2.0 microns, about 2.5 microns, about 3.0 microns, about 3.5 microns, about 4.0 microns, about 4.5 microns, about 5.0 microns, about 5.5 microns, about 6.0 microns, about 6.5 microns, about 7.0 microns, about 7.5 microns, about 8.0 microns, about 8.5 microns, about 9.0 microns, about 9.5 microns, or about 10.0 microns.

In certain embodiments of the invention, the non-solubilized fulvestrant particles have a CE Dn(10) between about 0.5 microns and about 2.0 microns, between about 0.5 microns and about 1.5 microns, between about 1.0 microns and about 1.5 microns, between about 0.8 microns and about 1.2 microns, between about 0.9 microns and about 1.1 microns, or between about 0.5 microns and about 1.0 microns. In other embodiments of the invention, the non-solubilized fulvestrant particles have a CE Dn(10) equal to about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0 microns.

In certain embodiments of the invention, the non-solubilized fulvestrant particles have a CE Dn(90) between about 4 microns and about 20 microns, a CE Dn(50) between about 2.0 microns and about 10.0 microns, and a CE Dn(10) between about 0.5 microns and about 2.0 microns. In other embodiments of the invention, the non-solubilized fulvestrant particles have a CE Dn(90) between about 6 microns and about 12 microns, a CE Dn(50) between about 2.0 microns and about 6.0 microns, and a CE Dn(10) between about 0.5 microns and about 1.5 microns. In further embodiments of the invention, the non-solubilized fulvestrant particles have a CE Dn(90) between about 8 microns and about 1 microns, a CE Dn(50) between about 3.0 microns and about 5.0 microns, and a CE Dn(10) between about 0.8 microns and about 1.2 microns.

Those skilled in the art will appreciate that numerous changes and modifications can be made to the preferred embodiments of the disclosure and that such changes and modifications can be made without departing from the spirit of the disclosure. It is, therefore, intended that the following examples and appended claims cover all such equivalent variations as fall within the true spirit and scope of the disclosure.

The disclosures of each patent, patent application, and publication cited or described in this document are hereby incorporated herein by reference, in its entirety.

EXAMPLES

Example 1: Analytical Methods

In some aspects, the amount of solubilized fulvestrant in aqueous suspensions was measured via HPLC analysis. Aqueous suspensions were filtered using 0.2 micron PVDF 25 mm syringe filters to remove particulates and filtered samples were directly injected into the HPLC apparatus for analysis. HPLC was performed with Agilent Technologies Agilent 1260 Infinity Quaternary LC module G1311B (Agilent Technologies, Santa Clara, Calif.). Other HPLC apparatuses may also be used to analyze solubilized fulvestrant concentrations.

In some aspects, particle size and particle size distributions were analyzed with Malvern Mastersizer 3000 (Malvern Instruments Ltd., Malvern, Worcestershire, UK) via laser diffraction. Reconstituted suspensions were analyzed as-is, or sonicated with an attached sample dispersion unit with an in-line sonication probe prior to analysis via laser diffraction.

In some aspects, particle size and particle size distributions were analyzed with Malvern Morphologi G3 (Malvern Instruments Ltd., Malvern, Worcestershire, UK), to determine circle equivalent (CE) diameters via microscopy image capture and analysis. CE diameters were measured and volume-weighted particle size distribution parameters were determined.

Example 2: In Vitro Analysis of Aqueous Fulvestrant Suspensions

Test vials of a lyophilized fulvestrant drug formulation were prepared consisting of fulvestrant, 500 mg; polysorbate 80, 25 mg; mannitol, 250 mg; and PLASDONE™ C-12 povidone, 8.0 mg, lyophilized from suspensions comprising Fulvestrant, USP 100 mg/mL, Polysorbate 80, NF: 0.5% (w/w), Mannitol, USP: 5.0% (w/w), PLASDONE™ C-12, NF (average MW=4000): 0.16% (w/w). In vitro analyses were performed on aqueous suspensions prepared with different aqueous diluents. Aqueous suspensions were prepared by slowly injecting the aqueous diluent into the test vial and gently swirling the vial by hand for five minutes to mix the suspension. Particle size, particle size distributions, and fulvestrant solubility were analyzed as noted in Tables 3-8 below.

TABLE 3

| Sample Diluent | "as is" LD measurement | | | sonicated LD measurement | | |
|---|---|---|---|---|---|---|
| | Dv(10) (μm) | Dv(50) (μm) | Dv(90) (μm) | Dv(10) (μm) | Dv(50) (μm) | Dv(90) (μm) |
| Water for Injection (WFI) Control | 2.19 | 8.35 | 43.1 | 1.44 | 5.02 | 10.2 |
| 0.9% NaCl | 1.94 | 9.26 | 54.5 | 1.31 | 4.61 | 9.52 |
| Bacteriostatic Water for Injection, USP (contains 0.9% benzyl alcohol) | 2.33 | 8.81 | 25.4 | 1.44 | 5.38 | 18.7 |
| Bacteriostatic 0.9% NaCl, USP (contains 0.9% benzyl alcohol) | 1.79 | 7.5 | 27.8 | 1.19 | 4.43 | 9.37 |
| PEG 300 5% aqueous | 2.34 | 9.15 | 41.4 | 1.37 | 4.87 | 9.98 |
| Propylene Glycol 2.5% | 2.3 | 8.32 | 38.2 | 1.37 | 4.87 | 9.98 |
| Polysorbate 20, 0.25% aq. | 1.81 | 6.57 | 37.3 | 1.02 | 3.19 | 6.89 |
| Polysorbate 80, 0.25% aq. | 1.93 | 6.85 | 33.5 | 1.25 | 4.2 | 8.55 |
| Lecithin, 0.3% aqueous | 2.08 | 7.13 | 32.1 | 1.15 | 3.6 | 7.31 |
| Ethanol, 5% aqueous | 1.99 | 7.18 | 27.5 | 1.35 | 4.95 | 10.2 |
| Tris buffer w Polysorbate 20 (pH 7.5: 0.05M Tris/Tris-HCl, 0.138M NaCl, 0.0027M KCl, Polysorbate 20, 0.05%) | 1.99 | 8.42 | n/a | 4.22 | 8.76 | 16.3 |

TABLE 4

| Diluent | Benzyl Alcohol % | Ethanol % | Polysorbate 20 % | Phosphate Buffer mM | Recon volume mL | "as is" LD measurement | | | sonicated LD measurement | | |
|---|---|---|---|---|---|---|---|---|---|---|---|
| | | | | | | Dv(10) (μm) | Dv(50) (μm) | Dv(90) (μm) | Dv(10) (μm) | Dv(50) (μm) | Dv(90) (μm) |
| WFI | 0 | 0 | 0 | 0 | 5 | 1.60 | 6.44 | 30.2 | 1.05 | 3.22 | 8.91 |
| WFI | 0 | 0 | 0 | 0 | 5 | 2.19 | 8.35 | 43.1 | 1.44 | 5.02 | 10.2 |
| Sterile WFI | 0.9 | 0 | 0 | 0 | 5 | 2.33 | 8.81 | 25.4 | 1.44 | 5.38 | 10.8 |
| Sterile NaCl | 0.9 | 0 | 0 | 0 | 5 | 1.94 | 9.26 | 54.5 | 1.31 | 4.61 | 9.52 |
| 7 | 2.0 | 0 | 0.50 | 0 | 5 | 2.72 | 8.45 | 16.6 | 1.14 | 3.86 | 7.96 |
| 8 | 2.5 | 0 | 0 | 0 | 5 | 2.52 | 7.81 | 15.7 | 1.21 | 4.64 | 9.67 |
| 10 | 1.2 | 0 | 0.75 | 5 | 5 | 2.04 | 8.60 | 23.0 | 1.04 | 3.52 | 7.34 |
| 22 | 0 | 8 | 0.75 | 0 | 5 | 1.96 | 6.96 | 24.1 | 1.13 | 3.72 | 7.59 |
| 23 | 0 | 4 | 0.75 | 0 | 5 | 1.80 | 6.03 | 23.6 | 1.04 | 3.28 | 6.79 |
| 24 | 0 | 2 | 0.25 | 5 | 5 | 1.75 | 6.06 | 23.0 | 1.22 | 4.09 | 8.38 |

TABLE 5

| Diluent | Recon Volume mL | Polysorbate 20, % | Ethanol % | Benzyl Alcohol, % | "as is" LD measurement | | | sonicated LD measurement | | |
|---|---|---|---|---|---|---|---|---|---|---|
| | | | | | Dv(10) (μm) | Dv(50) (μm) | Dv(90) (μm) | Dv(10) (μm) | Dv(50) (μm) | Dv(90) (μm) |
| Diluent A-1 | 3 mL | 0.75 | 4 | 0 | 1.71 | 5.86 | 20.9 | 1.04 | 3.44 | 7.28 |
| Diluent A-1 | 3 mL | 0.75 | 4 | 0 | 1.73 | 5.84 | 21.4 | 1.11 | 3.70 | 7.62 |
| Diluent A-2 | 3 mL | 0.75 | 4 | 3.6 | 2.71 | 7.45 | 15.3 | 1.21 | 4.30 | 8.81 |
| Diluent A-2 | 3 mL | 0.75 | 4 | 3.6 | 2.76 | 7.48 | 14.7 | 1.22 | 4.44 | 9.13 |
| Diluent A-5 | 3 mL | 1.50 | 4 | 0 | 1.75 | 5.92 | 23.2 | 1.00 | 3.25 | 6.78 |
| Diluent A-5 | 3 mL | 1.50 | 4 | 0 | 1.76 | 6.03 | 22.1 | 0.98 | 3.15 | 6.67 |
| Diluent A-6 | 3 mL | 1.50 | 4 | 3.6 | 2.61 | 7.16 | 14 | 1.14 | 3.94 | 8.24 |
| Diluent A-6 | 3 mL | 1.50 | 4 | 3.6 | 2.54 | 7.26 | 14.3 | 1.19 | 4.14 | 8.50 |

TABLE 6

| Diluent | CE measurement | | | "as is" LD measurement | | | sonicated LD measurement | | |
|---|---|---|---|---|---|---|---|---|---|
| | Dv(10) (μm) | Dv(50) (μm) | Dv(90) (μm) | Dv(10) (μm) | Dv(50) (μm) | Dv(90) (μm) | Dv(10) (μm) | Dv(50) (μm) | Dv(90) (μm) |
| 10 | 5.24 | 14.22 | 34.33 | 1.43 | 4.91 | 16.9 | 0.94 | 2.73 | 5.7 |
| 10 | 3.49 | 9.44 | 85.29 | 1.39 | 5.52 | 40.6 | 0.92 | 2.72 | 5.85 |
| 10 | 3.47 | 7.82 | 23.33 | 1.25 | 4.70 | 18.7 | 0.85 | 2.46 | 11.2 |

TABLE 7

| Diluent | Recon volume, mL | Benzyl Alcohol, % | Ethanol, % | Polysorbate 20, % | Phosphate Buffer, mM | Normalized Solubilized Fulvestrant relative to WFI, % |
|---|---|---|---|---|---|---|
| control (WFI) | 5 | 0 | 0 | 0 | 0 | 100 |
| 1 | 5 | 1.2 | 0 | 0.50 | 0 | 151.2 |
| 2 | 5 | 0 | 0 | 0.75 | 0 | 489.3 |
| 3 | 4.5 | 0 | 0 | 0.50 | 0 | 354.8 |
| 4 | 5 | 2.0 | 0 | 0.25 | 5 | 171.4 |
| 5 | 4 | 1.2 | 0 | 0 | 0 | 44.0 |
| 6 | 4 | 0 | 0 | 0.50 | 0 | 353.6 |
| 7 | 4 | 2.0 | 0 | 0.50 | 0 | 133.3 |
| 8 | 5 | 2.5 | 0 | 0 | 0 | 20.2 |
| 9 | 4.5 | 2.5 | 0 | 0.25 | 0 | 47.6 |
| 10 | 5 | 1.2 | 0 | 0.75 | 5 | 342.9 |
| 11 | 4 | 2.5 | 0 | 0.75 | 0 | 184.5 |
| 12 | 4 | 2.0 | 0 | 0.25 | 5 | 188.1 |
| 13 | 5 | 0 | 8 | 0.50 | 0 | 676.2 |
| 14 | 5 | 0 | 0 | 0.75 | 0 | 483.3 |
| 15 | 4.5 | 0 | 0 | 0.50 | 0 | 366.7 |
| 16 | 5 | 0 | 2 | 0.25 | 0 | 185.7 |
| 17 | 4 | 0 | 8 | 0 | 0 | 86.9 |
| 18 | 4 | 0 | 0 | 0.50 | 0 | 326.2 |
| 19 | 4 | 0 | 2 | 0.50 | 0 | 371.4 |
| 20 | 5 | 0 | 4 | 0 | 5 | 198.8 |
| 21 | 4.5 | 0 | 4 | 0.25 | 5 | 477.4 |
| 22 | 5 | 0 | 8 | 0.75 | 0 | 558.3 |
| 23 | 4 | 0 | 4 | 0.75 | 0 | 563.1 |
| 24 | 4 | 0 | 2 | 0.25 | 5 | 486.9 |

TABLE 8

| Diluent Name | Recon volume | Polysorbate 20, % | Ethanol, % | Benzyl Alcohol, % | Solubilized Fulvestrant (mg/mL) Assay |
|---|---|---|---|---|---|
| 23A | 3 mL | 0.75 | 3 | 0 | 0.0455 |
| 23B | 3 mL | 0.25 | 3 | 0 | 0.0189 |
| 23C | 3 mL | 0.5 | 3 | 0 | 0.0255 |
| 23D | 3 mL | 0.5 | 4 | 0 | 0.0313 |
| Diluent A-1 | 3 mL | 0.75 | 4 | 0 | 0.0383 |
| Diluent A-1 | 3 mL | 0.75 | 4 | 0 | 0.0383 |
| Diluent A-1 | 3 mL | 0.75 | 4 | 0 | 0.0458 |
| Diluent A-1 | 3 mL | 0.75 | 4 | 0 | 0.0357 |
| Diluent A-2 | 3 mL | 0.75 | 4 | 3.6 | 0.0000 |
| Diluent A-2 | 3 mL | 0.75 | 4 | 3.6 | 0.0006 |
| Diluent A-2 | 3 mL | 0.75 | 4 | 3.6 | 0.0006 |
| Diluent A-2 | 3 mL | 0.75 | 4 | 3.6 | 0.0006 |
| Diluent A-3 | 3 mL | 0.75 | 10 | 0 | 0.0473 |
| Diluent A-3 | 3 mL | 0.75 | 10 | 0 | 0.0436 |
| Diluent A-3 | 3 mL | 0.75 | 10 | 0 | 0.0504 |
| Diluent A-4 | 3 mL | 0.75 | 10 | 3.6 | 0.0041 |
| Diluent A-4 | 3 mL | 0.75 | 10 | 3.6 | 0.0025 |
| Diluent A-4 | 3 mL | 0.75 | 10 | 3.6 | 0.0148 |
| Diluent A-5 | 3 mL | 1.5 | 4 | 0 | 0.0778 |
| Diluent A-5 | 3 mL | 1.5 | 4 | 0 | 0.0802 |
| Diluent A-5 | 3 mL | 1.5 | 4 | 0 | 0.0804 |
| Diluent A-5 | 3 mL | 1.5 | 4 | 0 | 0.0847 |
| Diluent A-6 | 3 mL | 1.5 | 4 | 3.6 | 0.0242 |
| Diluent A-6 | 3 mL | 1.5 | 4 | 3.6 | 0.0194 |
| Diluent A-6 | 3 mL | 1.5 | 4 | 3.6 | 0.0238 |
| Diluent A-6 | 3 mL | 1.5 | 4 | 3.6 | 0.0225 |
| Diluent A-7 | 3 mL | 1.5 | 10 | 0 | 0.0633 |
| Diluent A-7 | 3 mL | 1.5 | 10 | 0 | 0.0553 |
| Diluent A-7 | 3 mL | 1.5 | 10 | 0 | 0.0808 |
| Diluent A-8 | 3 mL | 1.5 | 10 | 3.6 | 0.0472 |
| Diluent A-8 | 3 mL | 1.5 | 10 | 3.6 | 0.0444 |
| Diluent A-8 | 3 mL | 1.5 | 10 | 3.6 | 0.0284 |
| WFI | 3 mL | 0 | 0 | 0 | 0.0104 |
| WFI | 3 mL | 0 | 0 | 0 | 0.0147 |
| WFI | 3 mL | 0 | 0 | 0 | 0.0188 |

Example 3: Pharmacokinetic Study of Intramuscular Administration to Rats

A single dose intramuscular pharmacokinetic study in rats was performed with novel reconstituted suspensions of fulvestrant. Ten female Sprague-Dawley [Crl:CD®(SD)] rats/group received single intramuscular (IM) bolus doses of 15 mg/kg of novel reconstituted suspensions of fulvestrant or FASLODEX® (reference agent) into the large muscle mass in the left hind limb of each rat. The dose volume for the novel reconstituted suspensions was 0.15 mL/kg. The dose volume for FASLODEX® was 0.3 mL/kg. Based on body surface area, 15 mg/kg is approximately one-third of the recommended human dose of 500 mg/person/month. The rats were at least 10-13 weeks of age and weighed between 233-282 grams on Study Day 1 (day of dosing). The novel reconstituted suspensions of fulvestrant were formed from a lyophilized drug product consisting of fulvestrant, 500 mg; polysorbate 80, 25 mg; mannitol, 250 mg; and PLASDONE™ C-12 povidone, 8.0 mg, lyophilized from suspensions comprising Fulvestrant, USP 100 mg/mL, Polysorbate 80, NF: 0.5% (w/w), Mannitol, USP: 5.0% (w/w), PLASDONE™ C-12, NF (average MW=4000): 0.16% (w/w), referred to in Table 9 as "Test Product". The lyophilized drug product vials were reconstituted before administration with the diluents shown in Table 9 below. The commercially available FASLODEX® formulation was used as is and it is reported to contain 10% w/v Alcohol, USP; 10% w/v Benzyl Alcohol, NF; and 15% w/v Benzyl Benzoate, USP, in 100% w/v with Castor Oil, USP.

TABLE 9

| Group | Treatment | Number of Females | Formulation | Diluent | Volume (mL/vial) | Conc. (mg/mL) | Dose Level (mg/kg) | Dose Volume (mL/kg) |
|---|---|---|---|---|---|---|---|---|
| 1 | Comparative Agent- Single Dose | 10 | FASLODEX ®[A] | Castor oil | Not applicable | 50 | 15 | 0.30 |
| 2 | Test Article 1 | 10 | Test Product | WFI | 5 | 100 | 15 | 0.15 |
| 3 | Test Article 2 | 10 | Test Product | WFI | 5 | 100 | 15 | 0.15 |
| 4 | Comparative Agent- Split Dose | 10 | FASLODEX ®[A] | Castor Oil | Not applicable | 50 | 15[C] | 0.30[C] |
| 5 | Test Article 3 | 10 | Test Product | Diluent 23: 4% EtOH, 0.75% Polysorbate 20 | 5 | 100 | 15 | 0.15 |
| 6 | Test Article 4 | 10 | Test Product | Diluent 10: Benzyl alcohol NF:-12 mg/mL (1.2% w/w); Polysorbate 20, NF: 7.5 mg/mL (0.75% w/w); Monobasic Potassium phosphate, NF: 0.12 w/w %); Water for Injection, USP q.s. | 5 | 100 | 15 | 0.15 |
| 7 | Test Article 5 | 10 | Test Product | Diluent 24: 2% EtOH, 0.25% Polysorbate 20, 5 mM phosphate buffer | 5 | 100 | 15 | 0.15 |
| 8 | Test Article 6 | 10 | Test Product | Bacteriostatic Water for Injection (0.9% Benzyl Alcohol) | 5 | 100 | 15 | 0.15 |
| 9 | Test Article 7 | 10 | Test Product | Diluent 23: 4% EtOH, 0.75% Polysorbate 20 | 4 | 125 | 15 | 0.12 |
| 10 | Test Article 8 | 10 | Test Product | Bacteriostatic Water for Injection (0.9% Benzyl Alcohol) | 4 | 125 | 15 | 0.12 |
| 11 | Test Article 9 | 10 | Test Product | Diluent 23: 4% EtOH, 0.75% Polysorbate 20 | 3 | 166.7 | 15 | 0.09 |
| 12 | Test Article 4 | 10 | Test Product | Diluent 10: Benzyl alcohol NF: 12 mg/mL (1.2% w/w); Polysorbate 20, NF: 7.5 mg/mL (0.75% w/w); Monobasic Potassium phosphate, NF: 0.12 mg/mL (0.012 w/w %); Dibasic Potassium phosphate, USP: 0.71 mg/mL (0.071 w/w %); Water for Injection, USP q.s. | 4 | 125 | 15 | 0.12 |
| 13 | Test Article 4 | 10 | Test Product | Diluent 10: Benzyl alcohol NF: 12 mg/mL (1.2% w/w); Polysorbate 20, NF: 7.5 mg/mL (0.75% w/w); Monobasic Potassium phosphate, NF: 0.12 mg/mL (0.012 w/w %); Dibasic Potassium phosphate, USP: 0.71 mg/mL (0.071 w/w %); Water for Injection, USP q.s. | 3 | 166.7 | 15 | 0.09 |

[A]The commercially available FASLODEX ® formulation was used.
[C]The test article for Group 4 was split between two dose sites (left and right limb) and the Group received 7.5 mg/kg in each limb (total dose volume of 0.30 mL/kg (0.15 mL/kg/limb) and a total dose level of 15 mg/kg (7.5 mg/kg/limb)).

Blood collection time points for all rats were predose and 1, 3, 6, 12, 24, 48, 72, 120, 168, 216, 288, 360, 432, 576, 720, 888, 1056, and 1224 hours postdose. Plasma was obtained from blood samples and analyzed for fulvestrant concentration using a qualified assay. Formulation selection was based on pharmacokinetic data through 720 hours (30 days) post dose based on having captured an adequate portion of the terminal elimination phase. Pharmacokinetic parameters were calculated using model-independent methods for each animal and each group and included maximum observed plasma concentration ($C_{max}$), time of maximum observed plasma concentration ($T_{max}$), mean residence time from the time of dosing extrapolated to infinity ($MRT_{INF}$), adjusted Rsq ($R^2$), and area under the plasma concentration-time curve (AUC). The linear trapezoidal method was used for all animals having at least three consecutive quantifiable concentrations. Half-life values ($T_{1/2}$) was reported for each plasma concentration-time profile that had sufficient plasma concentrations in the terminal elimination phase (at least three samples not including $T_{max}$). Additional assessments included daily clinical observations and weekly body weights.

Mean pharmacokinetic parameters for Group 6, Diluent 10 in 5 mL volume, and FASLODEX® are shown in Table 10 below.

TABLE 10

Geometric Means (±standard deviation) for Pharmacokinetic Parameters following Single IM Injections of Aqueous Suspensions with Group 6, Diluent 10 (5 mL volume), or FASLODEX® in Rats

|  | $C_{max}$ (ng/mL) | $T_{max}$ (hr) | $T_{last}$ (hr) | $AUC_{0-720hr}$ (hr*ng/mL) | $T_{1/2}$ (hr) | $MRT_{INF}^b$ (hr) |
|---|---|---|---|---|---|---|
| Group 6: Diluent 10 (5 mL) | 22.2 ± 19.8 | 1-24 | 720 ± 720 | 4110 ± 1230 | 425 ± 267 | 609 ± 364 |
| FASLODEX® | 13.4 ± 3.17 | 1 ± 168 | 720 ± 720 | 4050 ± 615 | 605 ± 723 | 884 ± 985 |
| Group 6: Diluent 10: PK parameters expressed as % of Fulvestrant | 60.36% | NA | NA | 98.5% | 142.3% | 145.2% |

AUC parameters for Groups 5-13 are shown in Table 11 below.

TABLE 11

| Diluents | % of FASLODEX® Single-Dose AUC | | | | % of WFI Diluent (5 mL) AUC | | | |
|---|---|---|---|---|---|---|---|---|
|  | Day 1 24 hr | Day 9 216 hr | Day 18 432 hr | Day 30 720 hr | Day 1 24 hr | Day 9 216 hr | Day 18 432 hr | Day 30 720 hr |
| Group 5: Diluent 23, 5 mL | 58.08% | 77.96% | 81.19% | 87.83% | 113.50% | 129.50% | 120.60% | 130.50% |
| Group 6: Diluent 10, 5 mL | 64.23% | 91.94% | 95.38% | 98.54% | 125.60% | 152.70% | 141.70% | 146.40% |
| Group 7: Diluent 24, 5 mL | 59.62% | 74.73% | 85.15% | 89.29% | 116.50% | 124.10% | 126.50% | 132.60% |
| Group 8: Bacteriostatic WFI, 5 mL | 60.00% | 79.03% | 81.52% | 85.64% | 117.30% | 131.30% | 121.10% | 127.20% |
| Group 9: Diluent 23, 4 mL | 50.77% | 65.59% | 67.99% | 72.26% | 99.20% | 108.90% | 101.00% | 107.30% |
| Group 10: Bacteriostatic WFI, 4 mL | 53.46% | 62.90% | 65.35% | 70.07% | 104.50% | 104.50% | 97.10% | 104.10% |
| Group 11: Diluent 23, 3 mL | 53.85% | 61.83% | 66.34% | 72.26% | 105.30% | 102.70% | 98.50% | 107.30% |
| Group 12: Diluent 10, 4 mL | 83.46% | 84.11% | N/A | N/A | 163.14% | 139.74% | N/A | N/A |

TABLE 11-continued

| | % of FASLODEX ® Single-Dose AUC | | | | % of WFI Diluent (5 mL) AUC | | | |
|---|---|---|---|---|---|---|---|---|
| Diluents | Day 1 24 hr | Day 9 216 hr | Day 18 432 hr | Day 30 720 hr | Day 1 24 hr | Day 9 216 hr | Day 18 432 hr | Day 30 720 hr |
| Group 13: Diluent 10, 3 mL | 69.62% | 81.18% | N/A | N/A | 136.14% | 134.84% | N/A | N/A |

Blood plasma concentrations for Groups 1, 2, 3, 5, 6, 7, and 8 are shown graphically in the plot in FIG. 1.

Example 4: Pharmacokinetic Study of Intramuscular Administration in Humans

A single dose intramuscular pharmacokinetic study in human subjects was performed with novel reconstituted suspensions of fulvestrant. 600 healthy female subjects received single intramuscular (IM) doses of reconstituted suspensions of fulvestrant or FASLODEX® (reference agent) into the left or right dorsogluteal muscle area, randomized into the treatment groups in a 1:1 ratio. The study was conducted in healthy peri- and postmenopausal female subjects 40 to 75 years of age, with a body mass index of 18 kg/m² to 32 kg/m², and with a body weight of at least 50 kg at screening. Approximately half of the subjects were perimenopausal and half were post-menopausal. At least 20% of the randomized post-menopausal subjects were >65 years of age.

In subjects receiving the test product, reconstituted suspensions containing 500 mg (100 mg/mL) fulvestrant, 1×5 mL (500 mg) were injected over 1 minute into the right or left dorsogluteal muscle area on Day 1.[1] Other subjects received commercially available FASLODEX® (250 mg/5 mL) supplied in cartons containing 2 prefilled syringes each, which were injected slowly over 1 to 2 minutes into the right and left

[1] In other aspects, in subjects receiving the test product, reconstituted suspensions containing greater than 500 mg of fulvestrant, for example, up to about 3000 mg, are injected into the right or left dorsogluteal muscle area on Day 1.

dorsogluteal muscle area as 2×5 mL (500 mg) injections on Day 1. Blood samples were collected for PK analysis of fulvestrant at predose (within 60 minutes [min] prior to dosing) and at 3, 6, 12 h post-dose on Day 1, and on Days 2, 3, 4, 5, 6, 7, 8, 9, 10, 12, 15, 18, 21, 28, 35, 42, 49 56, 63, 70, 77, 84, 98, 112, 126 and 140. All PK samples collected from Days 2 to 10 were obtained within 1 hour of the dosing time on Day 1, within 3 hours of the dosing time on Days 12 to 21, within 4 hours of the dosing time on Days 28 to 84, and 1 day but within 6 hours of dosing time on Days 98 to 140. Plasma was harvested and analyzed for concentrations of fulvestrant using a validated liquid chromatography-tandem mass spectrometry method.

The test product in the study was provided in vials that needed reconstitution with diluent. After reconstitution with 5 mL of the provided diluent to obtain a fulvestrant concentration of 100 mg/mL in an aqueous suspension, a single 5 mL (500 mg) dose was administered intramuscularly with a 23-gauge needle (1.5-inch length) into the right or left dorsogluteal muscle area (Investigator's choice) on Day 1.[2] The reconstituted product was injected within 2 hours of preparation. The test product was stored refrigerated (2-8° C.).

The reconstituted suspensions of fulvestrant were formed from a lyophilized drug product with composition shown in Table 12, provided as a white to off-white colored lyophilized powder in a glass vial.

TABLE 12

| Ingredient | Quality Standard | mg/vial |
|---|---|---|
| Fulvestrant | USP/NF | 568 |
| Polysorbate 80 | USP/NF | 28.4 |
| Mannitol | USP/NF | 284 |
| Povidone | USP/NF | 9.1 |
| Water for Injection | USP/NF | 0.6 |

The lyophilized drug product vials were reconstituted before administration with 5.0 mL volume of the diluent shown in Table 13. Reconstitution was performed by mixing by hand using gentle swirling and gentle inversion of the glass vial.

[2] In other aspects, after reconstitution with the provided diluent to obtain a fulvestrant concentration of 100 mg/mL in an aqueous suspension, a single dose of greater than 500 mg of fulvestrant, for example up to 3000 mg of fulvestrant, is administered intramuscularly with a 23-gauge needle (1.5-inch length) into the right or left dorsogluteal muscle area (Investigator's choice) on Day 1.

TABLE 13

| Ingredient | Quality Standard | mg/vial | mg/mL |
|---|---|---|---|
| Benzyl Alcohol | USP/NF | 66 | 12 |
| Polysorbate 20 | USP/NF | 41.3 | 7.5 |
| Monobasic Potassium Phosphate | USP/NF | 0.67 | 0.12 |
| Dibasic Potassium Phosphate | USP/NF | 3.88 | 0.71 |
| Water for Injection | USP/NF | q.s. | q.s. |

The reconstituted suspension had the composition as shown in Table 14. The pH of the reconstituted suspension was approximately 7.6. Reconstitution suspension had a milky-white appearance.

TABLE 14

| Ingredient | mg/mL |
|---|---|
| Fulvestrant | 100 |
| Polysorbate 80 | 5 |
| Mannitol | 50 |
| Povidone | 1.6 |
| Benzyl Alcohol | 10.6 |
| Polysorbate 20 | 6.6 |
| Monobasic Potassium Phosphate | 0.11 |
| Dibasic Potassium Phosphate | 0.62 |
| Water for Injection, USP | q.s. to 1 mL |

The commercially available FASLODEX® formulation was stored in a refrigerator at 2° C. to 8° C. (36° F. to 46° F.) in its original carton until time of use, and was used as is. The FASLODEX® formulation is reported to contain 10% w/v Alcohol, USP; 10% w/v Benzyl Alcohol, NF; and 15% w/v Benzyl Benzoate, USP, in 100% w/v with Castor Oil, USP.

Plasma was separated out by centrifuging blood samples at 1800 g for 10 min and transferring 1 ml of supernatant plasma into a 2 mL cryovial stored at −20° C. until sent to the bioanalytical laboratory for determination of fulvestrant level.

All subjects who received study drug and had an adequate blood sampling to determine at least one PK parameter were included in the PK analysis. To qualify for the PK population, no more than one blood sample was missed during the first 15 days post-dose, and no more than two consecutive blood samples from Day 18 to Day 140.

Concentration data was summarized according to nominal (protocol-specified) sampling times. PK parameters were calculated using noncompartmental methods, and actual elapsed time from dosing was used to estimate individual plasma PK parameters. The overall exposure ($AUC_{last}$) of fulvestrant was compared between the 2 treatments, using an analysis of variance model. Analysis of variance using the general linear model method, was performed with log-transformed $AUC_{last}$ as the dependent variable and treatment group (Test or Reference) and dosing cohorts as fixed effects. Secondary PK parameter $C_{max}$ was evaluated by descriptive statistics. Area under the curve from time zero to the last measurable concentration ($AUC_{last}$) was calculated by the linear trapezoidal method. No concentration estimates were provided for missing sample values. Any sample with a missing value was treated as if the sample had not been scheduled for collection. If a subject had immediate predose (0-hour sample) levels that were greater than 5% of their measured $C_{max}$ value, the subject was excluded from the statistical analysis.

$AUC_{last}$ was log-transformed prior to analysis. Analyses of Variance (ANOVA) was performed using the General Linear Model (GLM) procedure of SAS with hypothesis testing for treatment effects at alpha=0.05. The statistical model contained main effects of treatment and dosing cohort. All effects were tested against the mean square error term from the ANOVA. Least square means for the treatments (LSMEANS statement), the difference between these means, the standard errors associated with the difference and the 90% confidence interval on the difference were obtained using the SAS ESTIMATE statement. The ratio of the test-to-reference geometric least squares means and the 90% confidence interval on the ratio was obtained by taking the antilog of the difference and 90% confidence interval on that difference. Comparisons of $C_{max}$ was performed on log-transformed data in the same way as described for $AUC_{last}$. Results are shown in Table 15. Table 15 shows calculated values for "RefLSM", which refers to the least square mean of the log-transformed measured value for all subjects treated with FASLODEX®, "RefGeoLSM", which refers to geometric least square mean of the measured value for all subjects treated with FASLODEX®, "TestLSM", which refers to the least square mean of the log-transformed measured value for all subjects treated with the reconstituted fulvestrant suspension test product, "TestGeoLSM", which refers to geometric least square mean of the measured value for all subjects treated with the reconstituted fulvestrant suspension test product. The row labeled "Ln($C_{max}$)" indicates $C_{max}$ values in ng/mL, log-transformed for columns where indicated. The row labeled "Ln(AUClast)" indicates AUClast values in day*ng/mL, log-transformed for columns where indicated. Arithmetic mean values and standard deviations for Cmax and AUClast were calculated for subjects treated with the test product (data included for n=291 subjects), with Mean Cmax=6.00 ng/mL (with SD of 7.47 ng/mL), and Mean AUClast=286 day*ng/mL (with SD of 101 day*ng/mL).

TABLE 15

| Analyte | Dependent | Ref LSM | Ref GeoLSM |
|---|---|---|---|
| Fulvestrant | Ln(Cmax) | 2.6156 | 13.6754 |
| Fulvestrant | Ln(AUClast) | 6.0573 | 427.2023 |

| Analyte | Dependent | Test LSM | Test GeoLSM |
|---|---|---|---|
| Fulvestrant | Ln(Cmax) | 1.6047 | 4.9764 |
| Fulvestrant | Ln(AUClast) | 5.5952 | 269.1225 |

| Analyte | Dependent | Ratio % Ref | CI 90% Lower | CI 90% Upper | Power | ANOVA CV % |
|---|---|---|---|---|---|---|
| Fulvestrant | Ln(Cmax) | 36.39 | 34.13 | 38.80 | 1.0000 | 22.02 |
| Fulvestrant | Ln(AUClast) | 63.00 | 60.35 | 65.75 | 1.0000 | 9.86 |

FIGS. 2-7 show linear and semi-logarithmic graphs of mean blood plasma concentrations of fulvestrant for the test product and FASLODEX®. The data points for mean blood plasma concentrations used in FIGS. 2-7 is shown in Table 16.

TABLE 16

| Days Post-Administration | Mean Plasma Fulvestrant Concentration (ng/mL) | | | |
|---|---|---|---|---|
| | Test Product | (n) | FASLODEX ® | (n) |
| 0.00 | 0.00 | 296 | 0.00 | 297 |
| 0.13 | 3.54 | 300 | 1.13 | 297 |
| 0.25 | 4.05 | 300 | 1.86 | 300 |
| 0.50 | 4.59 | 299 | 3.20 | 300 |
| 1.00 | 5.03 | 299 | 6.30 | 300 |
| 2.00 | 3.75 | 299 | 10.00 | 298 |
| 3.00 | 2.99 | 300 | 11.90 | 300 |
| 4.00 | 2.65 | 300 | 13.40 | 298 |
| 5.00 | 2.36 | 298 | 14.00 | 297 |
| 6.00 | 2.20 | 299 | 13.70 | 298 |
| 7.00 | 1.94 | 298 | 13.30 | 298 |
| 8.00 | 1.88 | 298 | 12.30 | 299 |
| 9.00 | 1.68 | 297 | 11.40 | 300 |
| 11.00 | 1.53 | 297 | 9.75 | 298 |
| 14.00 | 1.45 | 297 | 8.09 | 295 |
| 17.00 | 1.46 | 297 | 6.43 | 297 |
| 20.00 | 1.63 | 297 | 5.44 | 298 |
| 27.00 | 2.06 | 294 | 4.11 | 294 |
| 34.00 | 2.38 | 296 | 3.51 | 295 |
| 41.00 | 2.48 | 292 | 3.00 | 297 |
| 48.00 | 2.47 | 291 | 2.72 | 292 |
| 55.00 | 2.41 | 290 | 2.45 | 294 |
| 62.00 | 2.31 | 293 | 2.22 | 295 |
| 69.00 | 2.23 | 293 | 2.06 | 296 |
| 76.00 | 2.14 | 293 | 1.89 | 294 |
| 83.00 | 2.08 | 290 | 1.74 | 297 |
| 97.00 | 1.94 | 292 | 1.51 | 295 |
| 111.00 | 1.79 | 292 | 1.35 | 291 |
| 125.00 | 1.66 | 292 | 1.18 | 294 |
| 139.00 | 1.61 | 294 | 1.10 | 296 |

When ranges are used herein for chemical or physical properties, such as particle size or particle size distribution, formulation component concentrations, or pharmacokinetic properties, all combinations, and subcombinations of ranges for specific embodiments therein are intended to be included.

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of treating breast cancer in a subject, comprising administering to the subject an aqueous suspension comprising:
   solubilized fulvestrant;
   non-solubilized fulvestrant particles having one or more of:
      a laser diffraction diameter (10) (LD Dv(10)) between about 1.5 microns and about 2.1 microns,
      an LD Dv(50) between about 5.5 microns and about 9.0 microns, and
      an LD Dv(90) between about 15 microns and about 35 microns;
   a surfactant;
   a polyvinylpyrrolidone; and
   a sugar alcohol; and
   a water-soluble excipient that is:
      an aryl-$C_{1-6}$alk-OH,
      a $C_{1-6}$alkyl-OH,
      a buffering salt,
      a polysorbate,
      a polyalkylene glycol,
      a $C_{1-12}$alkylene glycol,
      a phosphatidylcholine,
      or a combination thereof.

2. The method of claim 1, wherein the breast cancer is hormone receptor (HR)-positive breast cancer.

3. The method of claim 1, wherein the subject is a post-menopausal human woman with disease progression following antiestrogen therapy.

4. The method of claim 2, wherein the breast cancer is HR-positive, human epidermal growth factor receptor 2 (HER2)-negative advanced or metastatic breast cancer.

5. The method of claim 1, wherein the subject is a human woman with disease progression after endocrine therapy.

6. The method of claim 1, wherein the administration is performed as a single intramuscular injection.

7. The method of claim 6, wherein the single intramuscular injection is administered to the ventrogluteal site or the dorsogluteal site.

8. The method of claim 1, wherein the administration is performed as two intramuscular injections.

9. The method of claim 1, wherein the administration is performed as a single subcutaneous injection.

10. The method of claim 1, wherein the administration is performed as two subcutaneous injections.

11. The method of claim 1, further comprising administering an additional therapeutic agents.

12. The method of claim 11, wherein the additional therapeutic agent is palbociclib.

13. The method of claim 1, wherein the aqueous suspension comprises between about 0.1% and about 5% (w/w), between about 0.5% and about 5% (w/w), between about 0.5% and about 2.5% (w/w), between about 0.9% and about 1.5% (w/w), about 4% (w/w), or about 1% (w/w) of the aryl-$C_{1-6}$alk-OH.

14. The method of claim 1, wherein the aryl-$C_{1-6}$alk-OH is benzyl alcohol.

15. The method of claim 1, wherein the aqueous suspension comprises between about 1% and about 10% (w/w), between about 5% and about 10% (w/w), between about 2% and about 4% (w/w), about 2% (w/w), about 4% (w/w), about 5% (w/w), or about 8% (w/w) of the $C_{1-6}$alkyl-OH.

16. The method of claim 1, wherein the $C_{1-6}$alkyl-OH is ethanol.

17. The method of claim 1, wherein the buffering salt is $NaH_2PO_4$, $K_2HPO_4$, $KH_2PO_4$, citric acid or a pharmaceutically acceptable salt thereof, tromethane or a pharmaceutically acceptable salt thereof, or a mixture thereof.

18. The method of claim 1, wherein the aqueous suspension comprises between about 0.1% to about 2% (w/w), between about 0.25% and about 1.80% (w/w), or about 0.75% (w/w), of the polysorbate.

19. The method of claim 1, wherein the polysorbate is polysorbate 20, polysorbate 60, polysorbate 80, or a combination thereof.

20. The method of claim 1, wherein the aqueous suspension comprises between about 1% and about 10% (w/w), between about 0.5% and about 8% (w/w), or about 5% (w/w) of the polyalkylene glycol.

21. The method of claim 1, wherein the polyalkylene glycol is a polyethylene glycol.

22. The method of claim 1, wherein the aqueous suspension comprises between about 0.1% and about 5% (w/w), between about 0.5% and about 4% (w/w), or about 2.5% (w/w) of the $C_{1-12}$alkylene glycol.

23. The method of claim 1, wherein the $C_{1-12}$alkylene glycol is propylene glycol.

24. The method of claim 1, wherein the aqueous suspension comprises between about 0.1% and about 5% (w/w), between about 0.1% and about 2% (w/w), or about 0.3% (w/w) of the phosphatidylcholine.

25. The method of claim 1, wherein the phosphatidylcholine is lecithin.

26. The method of claim 1, wherein the water soluble excipient is an aryl-$C_{1-6}$alk-OH, a $C_{1-6}$alkyl-OH, a polysorbate, or a buffering salt, or a combination thereof.

27. The method of claim 1, wherein the aqueous suspension has a pH of between about 6.0 and about 8.0, about 7, or about 7.5.

28. The method of claim 1, wherein the sugar alcohol is mannitol, xylitol, maltitol, lactitol, maltotriitol, sorbitol, glycerol, or a mixture thereof.

29. The method of claim 1, wherein the non-solubilized fulvestrant particles in the aqueous suspension have one or more of:
   a sonicated LD Dv(10) between about 1.0 microns and about 1.2 microns;
   a sonicated LD Dv(50) between about 3.0 microns and about 4.0 microns; and
   a sonicated LD Dv(90) between about 6 microns and about 9 microns.

30. The method of claim 1, wherein the non-solubilized fulvestrant particles in the aqueous suspension have one or more of:
   a circle equivalent (10) (CE Dv(10) between about 3.0 microns and about 6.0 microns;
   a CE Dv(50) between about 7.0 microns and about 16.0 microns; and
   a CE Dv(90) between about 20 microns and about 90 microns.

31. The method of claim 1, wherein upon administration of the aqueous suspension to a subject in a single intramuscular injection, the 90% confidence intervals (CI) of the relative mean AUC(0-t) and AUC(0-∞) of fulvestrant is within 80% to 125% of the relative mean AUC(0-t) and AUC(0-∞), respectively, of fulvestrant after administration of 500 mg of fulvestrant in the form of FASLODEX® administered intramuscularly as two 5 mL injections.

32. The method of claim 1, wherein upon administration of the aqueous suspension to a subject in a single intramuscular injection, the 90% confidence intervals (CI) of the relative mean AUC(0-t) and AUC(0-∞) of fulvestrant is within 90% to 110% of the relative mean AUC(0-t) and AUC(0-∞), respectively, of fulvestrant after administration of 500 mg of fulvestrant in the form of FASLODEX® administered intramuscularly as two 5 mL injections.

33. The method of claim 1, wherein upon administration of the aqueous suspension to a subject in a single intramuscular injection, the 90% confidence intervals (CI) of the relative mean Cmax of fulvestrant is within 40% to 80% of the relative mean Cmax of fulvestrant after administration of 500 mg of fulvestrant in the form of FASLODEX® administered intramuscularly as two 5 mL injections.

34. The method of claim 1, wherein upon administration of the aqueous suspension to a subject in two intramuscular injections, the 90% confidence intervals (CI) of the relative mean AUC(0-t) and AUC(0-∞) of fulvestrant is within 80% to 125% of the relative mean AUC(0-t) and AUC(0-∞), respectively, of fulvestrant after administration of 500 mg of fulvestrant in the form of FASLODEX® administered intramuscularly as two 5 mL injections.

35. The method of claim 1, wherein upon administration of the aqueous suspension to a subject in two intramuscular injections, the 90% confidence intervals (CI) of the relative mean AUC(0-t) and AUC(0-∞) of fulvestrant is within 90% to 110% of the relative mean AUC(0-t) and AUC(0-∞), respectively, of fulvestrant after administration of 500 mg of fulvestrant in the form of FASLODEX® administered intramuscularly as two 5 mL injections.

36. The method of claim 1, wherein upon administration of the aqueous suspension to a subject in two intramuscular injections, the 90% confidence intervals (CI) of the relative mean Cmax of fulvestrant is within 40% to 80% of the relative mean Cmax of fulvestrant after administration of 500 mg of fulvestrant in the form of FASLODEX® administered intramuscularly as two 5 mL injections.

37. The method of claim 1, wherein the aqueous suspension has a volume of between about 3.0 mL and about 6.0 mL or about 5 mL.

38. The method of claim 1, wherein the aqueous suspension has a volume of between about 8.0 mL and about 12.0 mL or about 10.0 mL.

39. The method of claim 1, wherein the total amount of fulvestrant from solubilized fulvestrant and non-solubilized fulvestrant particles in the aqueous suspension is between about 80 mg/mL and about 170 mg/mL or about 100 mg/mL.

40. The method of claim 1, wherein the administering comprises administering:
a first dose with a first-dose fulvestrant amount on day 1;
a second dose with a second-dose fulvestrant amount after a first time period subsequent to the first dose; and
one or more additional doses with a third-dose fulvestrant amount after a second time period subsequent to the second dose and repeated at a frequency of one dose per a third time period.

41. The method of claim 40, wherein the first-dose fulvestrant amount comprises between about 500 mg and about 3000 mg, between about 500 mg and about 1500 mg, between about 750 mg and about 1500 mg, between about 750 mg and about 1250 mg, between about 750 mg and about 1000 mg, between about 800 mg and about 1200 mg, between about 850 mg and about 1150 mg, between about 900 mg and about 1100 mg, between about 950 mg and about 1050 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of fulvestrant.

42. The method of claim 40, wherein the second-dose fulvestrant amount comprises between about 500 mg and about 3000 mg, between about 500 mg and about 1500 mg, between about 750 mg and about 1500 mg, between about 750 mg and about 1250 mg, between about 750 mg and about 1000 mg, between about 800 mg and about 1200 mg, between about 850 mg and about 1150 mg, between about 900 mg and about 1100 mg, between about 950 mg and about 1050 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of fulvestrant.

43. The method of claim 40, wherein the third-dose fulvestrant amount comprises between about 500 mg and about 3000 mg, between about 500 mg and about 1500 mg, between about 750 mg and about 1500 mg, between about 750 mg and about 1250 mg, between about 750 mg and about 1000 mg, between about 800 mg and about 1200 mg, between about 850 mg and about 1150 mg, between about 900 mg and about 1100 mg, between about 950 mg and about 1050 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, or about 1500 mg of fulvestrant.

44. The method of claim 40, wherein the first time period comprises between about 1 day and about 30 days, between about 5 days and about 25 days, between about 10 days and about 20 days, between about 10 days and about 15 days, between about 12 days and about 16 days, between about 13 days and about 15 days, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days.

45. The method of claim 40, wherein the second time period comprises between about 1 day and about 30 days, between about 5 days and about 25 days, between about 10 days and about 20 days, between about 10 days and about 15 days, between about 12 days and about 16 days, between about 13 days and about 15 days, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days.

46. The method of claim 40, wherein the third time period comprises between about 1 days and about 90 days, between about 60 days and about 90 days, between about 75 days and about 90 days, between about 30 days and about 60 days, between about 45 days and about 60 days, between about 45 days and about 75 days, between about 50 days and about 70 days, between about 55 days and about 65 days, between about 10 days and about 50 days, between about 15 days and about 45 days, between about 20 days and about 40 days, between about 25 days and about 35 days, between about 5 days and about 35 days, between about 10 days and about 30 days, between about 15 days and about 25 days, between about 1 weeks and about 12 weeks, between about 6 weeks and about 12 weeks, between about 7 weeks and about 12 weeks, between about 8 weeks and about 12 weeks, between about 9 weeks and about 12 weeks, between about 10 weeks and about 12 weeks, between about 11 weeks and about 12 weeks, between about 4 weeks and about 10 weeks, between about 5 weeks and about 10 weeks, between about 6 weeks and about 10 weeks, between about 7 weeks and about 10 weeks, between about 8 weeks and about 10 weeks, between about 9 weeks and about 10 weeks, between about 2 weeks and about 8 weeks, between about 3 weeks and about 8 weeks, between about 4 weeks and about 8 weeks, between about 5 weeks and about 8 weeks, between about 6 weeks and about 8 weeks, between about 7 weeks and about 8 weeks, between about 1 weeks and about 6 weeks, between about 2 weeks and about 6 weeks, between about 3 weeks and about 6 weeks, between about 4 weeks and about 6 weeks, between about 5 weeks and about 6 weeks, between about 1 weeks and about 4 weeks, between about 2 weeks and about 4 weeks, between about 3 weeks and about 4 weeks, between about 1 weeks and about 3 weeks, between about 2 weeks and about 3 weeks, between about 1 months and about 3 months, between about 2 months and about 3 months, between about 1.5 months and 2.5 months, between about 1.5 months and 3.5 months, between about 2.0 months and about 3.5 months, between about 2.0 months and about 2.5 months, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, about 50 days, about 51 days, about 52 days, about 53 days, about 54 days, about 55 days, about 56 days, about 57 days, about 58 days, about 59 days, about 60 days, about 61 days, about 62 days, about 63 days, about 64 days, about 65 days, about 66 days, about 67 days, about 68 days, about 69 days, about 70 days, about 71 days, about 72 days, about 73 days, about 74 days, about 75 days, about 76 days, about 77 days, about 78 days, about 79 days, about 80 days, about 81 days, about 82 days, about 83 days, about 84 days, about 85 days, about 86 days, about 87 days, about 88 days, about 89 days, about 90 days, about 1 month, about 1.5 months, about 2 months, about 2.5 months, about 3 months, or about 3.5 months.

47. The method of claim 40, wherein:
the first-dose fulvestrant amount comprises between about 750 mg and about 1250 mg of fulvestrant;
the second-dose fulvestrant amount comprises between about 750 mg and about 1250 mg of fulvestrant;
the first time period is about 14 days;
the third-dose fulvestrant amount comprises about 500 mg of fulvestrant;
the second time period is about 14 days; and
the third time period is about 2 months.

48. The method of claim 40, wherein:
the first-dose fulvestrant amount comprises between about 750 mg and about 1250 mg of fulvestrant;
the second-dose fulvestrant amount comprises between about 750 mg and about 1250 mg of fulvestrant;
the first time period is about 14 days;
the third-dose fulvestrant amount comprises about 500 mg of fulvestrant;
the second time period is about 14 days; and
the third time period is about 1 month.

49. The method of claim 47, wherein the first-dose fulvestrant amount comprises between about 750 mg and about 1000 mg of fulvestrant.

50. The method of claim 47, wherein the second-dose fulvestrant amount comprises between about 750 mg and about 1000 mg of fulvestrant.

51. The method of claim 47, wherein the first-dose fulvestrant amount comprises about 1000 mg of fulvestrant.

52. The method of claim 47, wherein the second-dose fulvestrant amount comprises about 1000 mg of fulvestrant.

53. The method of claim 47, wherein the first-dose fulvestrant amount comprises about 1500 mg of fulvestrant.

54. The method of claim 47, wherein the second-dose fulvestrant amount comprises about 1500 mg of fulvestrant.

55. The method of claim 47, wherein the first-dose fulvestrant amount comprises about 2000 mg of fulvestrant.

56. The method of claim 47, wherein the second-dose fulvestrant amount comprises about 2000 mg of fulvestrant.

* * * * *